US007016462B1

(12) United States Patent
Keville et al.

(10) Patent No.: US 7,016,462 B1
(45) Date of Patent: Mar. 21, 2006

(54) IONIC PRE-CONCENTRATION XRF IDENTIFICATION AND ANALYSIS DEVICE, SYSTEM AND METHOD

(75) Inventors: Robert F. Keville, Valley Springs, CA (US); Daniel D. Dietrich, Livermore, CA (US)

(73) Assignees: InterScience, Inc., Troy, NY (US); KMD Science, Inc., Valley Springs, CA (US)

( * ) Notice: Subject to any disclaimer, the term of this patent is extended or adjusted under 35 U.S.C. 154(b) by 0 days.

(21) Appl. No.: 10/065,683

(22) Filed: Nov. 8, 2002

(51) Int. Cl.
   *G01N 23/223* (2006.01)
(52) U.S. Cl. .............................. 378/47; 378/45; 378/48
(58) Field of Classification Search ................ 378/44, 378/45, 47, 48, 53, 83, 88; 356/36, 38, 244, 356/246, 317, 318, 436, 437, 440, 441, 442, 356/445; 250/461.2
See application file for complete search history.

(56) References Cited

U.S. PATENT DOCUMENTS

| | | | | |
|---|---|---|---|---|
| 4,134,012 A | * | 1/1979 | Smallbone et al. ........... | 378/47 |
| 4,388,530 A | * | 6/1983 | Lubecki et al. ............... | 378/45 |
| 4,467,206 A | * | 8/1984 | Taylor et al. ................ | 250/435 |
| 4,979,198 A | * | 12/1990 | Malcolm et al. ............ | 378/102 |
| 5,192,432 A | | 3/1993 | Andelman ................... | 204/665 |
| 5,200,068 A | | 4/1993 | Andelman ................... | 204/645 |
| 5,349,624 A | * | 9/1994 | Warren et al. ................ | 378/43 |
| 5,360,540 A | | 11/1994 | Andelman ............... | 210/198.2 |
| 5,415,768 A | | 5/1995 | Andelman ............... | 210/198.2 |
| 5,425,858 A | | 6/1995 | Farmer ....................... | 204/450 |
| 5,503,004 A | * | 4/1996 | Agar ......................... | 73/61.44 |
| 5,538,611 A | | 7/1996 | Otowa ........................ | 204/550 |
| 5,547,581 A | | 8/1996 | Andelman .................. | 210/656 |
| 5,608,774 A | * | 3/1997 | Polichar et al. ............. | 378/102 |
| 5,620,597 A | | 4/1997 | Andelman ............... | 210/198.2 |
| 5,779,891 A | | 7/1998 | Andelman ............... | 210/198.2 |
| 5,834,633 A | | 11/1998 | Davison ..................... | 73/53.01 |
| 5,945,084 A | | 8/1999 | Droege ..................... | 423/447.4 |
| 5,954,937 A | | 9/1999 | Farmer ....................... | 205/687 |
| 5,982,847 A | * | 11/1999 | Nelson ........................ | 378/47 |
| 6,012,325 A | * | 1/2000 | Ma ............................. | 73/24.02 |

(Continued)

FOREIGN PATENT DOCUMENTS

JP            01214748 A    *   8/1989

OTHER PUBLICATIONS

Kump et al., "Determination of Trace Elements in Mineral Water Using Total Reflection X-ray Fluorescence Spectrometry after Preconcentration with Ammonium Pyrrolidinedithiocarbamate", X-ray Spectrometry, 1997, vol. 26, pp. 232-236.*

*Primary Examiner*—Edward J. Glick
*Assistant Examiner*—Chih-Cheng Glen Kao
(74) *Attorney, Agent, or Firm*—Jay R. Yablon; Michelle D. Simkulet

(57) ABSTRACT

A device, system and method for detecting and measuring concentrations of elements in fluids comprises: flowing a fluid through a central flow interelectrode gap of an ionic preconcentration cell separating an upper high specific surface area electrode from a lower high specific surface area electrode of the ionic preconcentration cell by a predetermined interelectrode gap width; and applying a voltage differential between the upper high surface area electrode and the lower high surface area electrode while the fluid is flowing through the central flow interelectrode gap. As such, this cell that utilizes its inherent capacitance for double layer formation to extract ultra-trace levels of ionic contaminants from fluids in order to enhance detection by x-ray fluorescence analysis.

147 Claims, 15 Drawing Sheets

U.S. PATENT DOCUMENTS

| | | | |
|---|---|---|---|
| 6,045,685 A * | 4/2000 | Fajt et al. | 205/701 |
| 6,148,061 A * | 11/2000 | Shefer et al. | 378/121 |
| 6,309,532 B1 * | 10/2001 | Tran et al. | 205/687 |
| 6,349,128 B1 * | 2/2002 | Nelson | 378/44 |
| 2002/0051898 A1 * | 5/2002 | Moulthrop et al. | 429/17 |
| 2004/0132845 A1 * | 7/2004 | Rhine et al. | 521/82 |

* cited by examiner

IONIC PRE-CONCENTRATION XRF IDENTIFICATION AND ANALYSIS DEVICE, SYSTEM AND METHOD

BACKGROUND OF INVENTION

This invention relates to the field of x-ray fluorescence analysis systems with pre-concentration devices, particularly for the in-situ measurement of ultra-trace levels of ionic contaminants in aqueous solutions.

Virtually all elements in the periodic table form compounds that are soluble in water. Dissolved impurities exist in aqueous streams as positive and negative charged pairs of anions and cations. Many of these impurities are toxic for human consumption or harmful to industrial processes. Therefore, the detection and quantitative measurement of the concentration of these impurities is of interest.

The present invention was developed to assist industries which have a continuous need to in-situ monitor effluent discharges to sanitary systems, and industries within the manufacturing arena where ultra pure fluids are required, such as for the production of microchips, or where fairly precise concentrations of trace elements within fluids are desired. This invention is also useful to ensure the quality and purity of intake or supply waters more generally to meet health and environmental standards. Current methodologies for the detection of trace materials, e.g., trace metals and other ionic components within process fluid streams, typically require samples to be prepared for off line analysis by specialized laboratories, which can be both costly and time consuming. Valuable production time is lost while waiting for results of required tests, or worse, when unacceptable concentrations are allowed to pass through the system for lack of continuous, on-line monitoring capability.

The usage of x-ray fluorescence (XRF) as an analytical method is well known to those skilled in the art. The XRF technique uses x-rays from a source directed towards the sample which are absorbed by the atoms in the sample. If the primary x-ray energy is sufficient, electrons in the atom are ejected from the higher binding energy inner shells creating vacancies and leaving the atom in an excited state. As the vacancy is filled by electrons from the lower binding energy outer shells, a photon with energy equal to the difference in the binding energy of the outer and inner shell electrons is ejected from the atom. Each element in the periodic chart has a unique set of energy levels, thereby allowing for identification of its presence through analysis of the energy of the emitted photon. The rate at which such photons are detected can be related to their concentration. In general, the higher the atomic number of the element, the more energetic are its characteristic fluorescence photons. By examining the intensity of the energy spectrum of the detected photons, the technique is capable of non-destructively determining the relative elemental composition of a sample. Because the emitted photons are attenuated by intervening materials between the sample and the detector, the technique is generally incapable of detecting low-atomic number (Z) elements below neon (Z=10) with energies less than 1 keV.

XRF spectroscopy has been utilized for several decades in the analysis of fossil fuels, food products such as cooking oils, soft drinks, wastewater, drinking water and medical fluids. Typical XRF processing requires the gathering of sample material so that it can be inserted into the instrument.

The sensitivity of XRF techniques depends upon the achievable signal to noise ratio. This is determined by the number of photons emitted from the element of interest at its characteristic x-ray energy that can be detected compared to photons of nearby energies scattered into the detector via other processes. Because the background is randomly distributed, the signal to noise ratio can be improved by extending the exposure time. A carefully constructed standard XRF unit is able to achieve sensitivity of about 1 to 10 parts-per-million (ppm) in mass ratio with about 30 minutes of exposure. However, to improve that sensitivity by a factor of two statistically requires a factor of four times as long a time, i.e., sensitivity improvement varies only with the square root of time. Therefore, to detect trace-level impurities at sub-ppm, the exposure times required would be inordinately long. Long exposure time usually introduces other non-statistical limitations, such as, but not limited to, gain drift in the detector, source output stability, etc. Thus, for all practical purposes, real-time analysis by direct XRF technique is limited to the ppm level since any greater sensitivity requires exposure times in excess of a few hours.

For quantitative work at better (greater sensitivity) than the 1–10 ppm level, processing of the material by means such as leaching, filtration, surface treatments, etc., by a highly trained individual is required to control "matrix" effects. This can take from several hours to days. This lengthy time between collection and reporting of analytical results prohibits XRF from being considered a 'real time' analytical method at ppm or better sensitivity levels.

The detection sensitivity can be improved by pre-concentrating the sample. Various filtration techniques have been tried for the detection of impurities associated with particulate matters, and ion exchange and chelating membranes have been utilized for the pre-concentration of dissolved compounds. These techniques typically require complex reversal processes such as removal or cleansing of a filter or drastically changing the pH of an ion exchange bed, for example. The capability to perform these pre-concentration steps and the subsequent analyses in-situ generally requires intervention of highly trained personnel and is not easily automated for on-site, real-time measurements.

Technologies used for extracting trace materials such as trace metals and ionic components in flow streams are often based upon or incorporated into water purification technologies. For example, U.S. Pat. Nos. 5,954,937 and 5,425,858 both by Farmer disclose an electrochemical cell for the removal of dissolved impurity ions from a liquid medium for purification purposes. The invention makes use of a highly porous carbon aerogel with very high surface density to form the electrodes of a capacitor. Upon the application of a bias voltage, the dissolved ions are attracted to the respective electrodes where they are captured in a "double layer" structure. The process can be reversed electrically to regenerate the cell. The concept is similar to earlier patents by Andelman (U.S. Pat. Nos. 5,192,432, 5,200,068, 5,360,540, 5,415,768) that make use of a carbon fiber as the porous material wherein the capacitor is wound in a spiral configuration for the fluid to flow through the electrodes, whereas Farmer uses a stack of capacitors requiring the fluid to flow between the electrodes. Farmer also recognizes that upon regeneration, the ions captured in the double layer can be discharged to a secondary chamber with significantly higher concentration to facilitate detection (see U.S. Pat. No. 5,954,937, column 27, line 43 through column 28, line 7). But, Farmer provides no disclosure on specific arrangements for in-situ or remote measurements, nor on how to configure and operate a cell for such measurements, nor on how quantitative information regarding the concentration of the impurities in the flow stream can be determined. Clearly Farmer has not considered all of the technical issues that need to be resolved in order to obtain quantitative, in-situ or remote measurements of trace level impurity concentration in a flow stream.

For detection of trace level impurities in flow streams, additional prior art is found in chemical based concentration systems. U.S. Pat. No. 5,834,633 by Davison claims the use of a permeable membrane capable of binding the impurity as a sampling device to collect and concentrate metal ions to facilitate detection using laboratory equipment such as is used in proton-induced X-ray emission (PIXE) techniques.

The prior art described above would be improved upon by an apparatus and method which provides a pre-concentration device capable of providing fully automated in-situ or remote analysis in real-time to provide quantitative measurements of trace materials in a fluid matrix, across a broad range of elements and concentration levels, by using well established XRF techniques but with significantly greater sensitivity than is made possible using standard XRF techniques and measurements.

SUMMARY OF INVENTION

The invention disclosed herein comprises a pre-concentration cell that can be integrated with an x-ray fluorescence analysis system to achieve significantly improved sensitivity in the detection and measurement of trace element concentrations in flow streams (elements in fluids). The device, system and method herein disclosed is capable of being implemented on-line for fully automated, in-situ, quantitative measurements of these trace element concentrations in flow streams. The concentrations of these impurities are usually reported in parts-per-million (ppm) or parts-per-billion (ppb) of mass units, or equivalently as microgram/gram for ppm, and nanogram/gram for ppb. At such low concentrations, the detection and quantitative measurement of these impurities is nontrivial, and requires novel and non-obvious devices, systems, and methods.

It is important at the outset to distinguish the removal of impurities from the detection and measurement of impurities. For the detection and quantitative measurement of impurity concentrations by X-ray fluorescence, where the objective is to obtain a quantitatively accurate concentration measurement, the design and operation of a concentration cell must be significantly different than for desalinization, or deionization more generally, where the objective is to saturate the electrode surfaces in order to maximally remove all dissolved ions.

In general, the ability to detect an element present in trace amounts is determined by the intensity of the characteristic signal above background noise. The signal intensity is directly proportional to the concentration of the element, whereas the background noise arises from all other sources. The pre-concentration cell extracts ultra-trace levels of ionic contaminants from aqueous solutions in order to bring the intensity of the signal above background noise, so it becomes detectable by XRF or similar techniques.

Because most dissolved impurities exist as charged pairs, they can be concentrated by flowing the liquid in which they are contained through an energized capacitor. This process is commonly known as "capacitive deionization." The charged particles are drawn toward the positive and negative electrodes at a rate determined by their respective mobility in the solution and are captured by the respective electrodes to form what is known as a double layer. The amount of charge that can be collected is determined by the surface area available on the electrodes. This fact is exploited in the capacitive deionization processes to remove dissolved impurities from water, such as those disclosed in the patents by Andelman (U.S. Pat. Nos. 5,192,432, 5,200,068, 5,360,540, 5,415,768, 5,547,581, 5,620,597, 5,779,891), Farmer (U.S. Pat. Nos. 5,425,858, 5,954,937) and Otowa (U.S. Pat. No. 5,538,611).

If this flow were to be continued indefinitely, more and more of the anions and cations would become attached to the surface of the electrodes. Eventually, saturation would occur when the total charge on the electrode equals the ratio of the capacitance of the capacitor over the applied potential. Once saturated, while there is no further net charge buildup, an ion exchange process would continue through which high valence state ions replace low valence state ions in the double layer. By allowing this process to continue, eventually, the high valence state ions would be preferentially captured by the double layers in the electrode. Ordinarily, the desired data is acquired long before saturation, though in some circumstances, saturation may be desirable.

Because the capacitance of a capacitor is proportional to the surface area available for collection of charges, electrodes made of porous, pervious material with large surface to volume ratio are capable of holding significantly more electrical charges before reaching saturation than non-pervious materials. For application as electrodes, the material must also be electrically conducting. One such material is carbon in the forms of fiber or porous foam. A type of carbon foam known as aerogel can achieve surface density as high as $10^3$ m$^2$/gm, consisting of ultra-fine cells with average pore sizes of less than 50 nm. In general, the higher the density of pores and the smaller the pore size, the higher the surface density in area per mass unit. This aerogel material is extensively used as the electrode material for ultra-capacitors. Farmer's patent for desalinization based on the capacitive deionization process uses this aerogel material.

The basic invention comprises a single capacitor with two electrodes made of porous, low atomic number conducting material with very high surface density separated by a small gap to form a flow channel for the fluid being characterized. The pressure and flow rate of the sample fluid must be carefully regulated and optimized for purpose of enhanced detection and quantification, rather than deionization. With the application of a voltage to the electrodes, the dissolved ions are collected on the surface of the electrodes to build up the concentration needed for detection by XRF or similar technique. Upon shorting out the electrodes, all the captured ions are returned into the flow stream. The process, therefore, is reversible, and the preconcentration cells are reusable.

In general, the XRF technique requires a source to illuminate the sample with primary X-rays. In the present case, the sample comprises the electrodes of the capacitor with the captured impurity ions. Upon excitation by the primary X-ray, the impurity ions will fluoresce with emissions of photons of their characteristic energy. A detector capable of resolving the energy of the photons must be properly situated to collect the emitted photons. The measured intensity in each energy channel is then related to the concentration of the impurity on the electrode. The procedure for deducing quantitative information on the concentration of the impurities in the flow stream from the measurements is an important part of this invention.

Because the electrode material is porous, it must be enclosed by a non-porous material of sufficient strength to contain the flow pressure. On the other hand, the X-ray source and the detector must be situated outside the flow enclosure. The presence of the enclosure attenuates both the incident primary x-ray and the emitted secondary fluoresce photons. This is not a problem when the purpose is removal, e.g., deionization only. But for quantitative XRF analysis, inattention to the enclosure design will significantly reduce the sensitivity of the XRF technique. Therefore, the enclosure must be designed with a window that is highly transparent to the fluoresce photons. The design of the window and selection of suitable material for the window is also and important part of this invention.

From signal to noise considerations, it is desirable that the sample being measured contain a minimum of intervening materials in the path of the primary X-ray and the secondary fluorescence photons. In the present case, the intervening materials includes the cell window for passage of the X-rays, the electrode material, and the contained fluid ("matrix") being tested. The design of the concentration cell to enhance the signal to noise ratio is also an important part of this invention.

As will be discussed, it is also important to extract only a small percentage of impurities from the flow stream, and the flow rate must be carefully established and controlled to achieve this objective. Thus, determining and controlling a suitable flow rate of the fluid through the preconcentration cell is also an important part of this invention.

The present invention is intended for utilization both at the source point for on-line installation and real-time measurements, as well as for measurements of samples taken with the concentration cell at remote sites and then transported to an analysis site. The present invention also allows the measurements and analysis to be made automatically without operator interventions, and the system can be maintained by personnel with no prior knowledge of x-ray science, x-ray fluorescence techniques or chemistry. Because this can be implemented as an automated system, the data can be recorded or reported remotely via wired or wireless transmissions. All these capabilities represent significant novel and non-obvious improvements over current technologies.

A preferred system for detecting and measuring concentrations of elements in fluids in accordance with the invention makes use of an ionic preconcentration cell comprising: an upper high surface area electrode comprising a high specific surface area thereof; a lower high surface area electrode comprising a high specific surface area thereof, substantially parallel to the upper high surface area electrode; a central flow interelectrode gap separating the upper and lower high surface area electrodes by a predetermined interelectrode gap width; and fluid flow means for flowing the fluid through the central flow interelectrode gap. Also important is voltage application means for applying a voltage differential between the upper high surface area electrode and the lower high surface area electrode while the fluid is flowing through the central flow interelectrode gap, though it is understood that a suitable ionic preconcentration cell might be manufactured without the voltage application means, with the voltage application means subsequently added before the cell is used.

A preferred method for detecting and measuring concentrations of elements in fluids in accordance with the invention comprises the steps of: flowing a fluid through a central flow interelectrode gap of an ionic preconcentration cell separating an upper high specific surface area electrode from a lower high specific surface area electrode of the ionic preconcentration cell by a predetermined interelectrode gap width; and applying a voltage differential between the upper high surface area electrode and the lower high surface area electrode while the fluid is flowing through the central flow interelectrode gap.

Therefore, it is desirable to provide a system that is configured and optimized for quantitative detection and measurement of trace elements rather than removal of such trace elements, that can achieve higher sensitivity across a broader range of low-concentration levels.

In particular, it is desirable for such a system to have a support structure that allows better penetration by x-rays or other radiation used for analysis, that avoids the entraining of excess fluids which can hinder the full range and sensitivity of detection, and that uses electrode materials better suited to detection and measurement rather than to removal of trace material concentrations.

It is also desirable to provide optimum flow rates and pressures for the purpose of detecting and measuring rather than removing trace elements.

It is also desirable to provide a system which substantially replaces trace elements back into the flow stream from whence they came, once detection is complete.

It is also desirable to provide an x-ray fluorescence analysis system with an integrated ionic pre-concentration device.

It is also desirable to provide for a portable, in-situ, x-ray fluorescence analysis system with an integrated ionic pre-concentration device.

It is also desirable to provide for a stand-alone concentration cell that can be used to sample a flow stream for remote, off-line utilization, wherein the cell can later be transported to an x-ray source for measurement and analysis of the impurity concentrations in the flow stream, which is again optimized for XRF measurement rather than removal.

It is also desirable to provide for a method of analyzing multiple species dissolved ionic concentrations, for purposes of both species identification and quantitative measurement of each species, as desired.

It is also desirable to provide for the ability to perform such an analysis by remote telecommunications utilizing technology such as wireless transmission or the Internet.

It is also desirable to provide for a system which can be operated by lay personnel without advanced scientific training.

BRIEF DESCRIPTION OF DRAWINGS

The features of the invention believed to be novel are set forth in the associated claims. The invention, however, together with further objects and advantages thereof, may best be understood by reference to the following description taken in conjunction with the accompanying drawings in which:

DETAILED DESCRIPTION

The invention disclosed herein comprises a pre-concentration cell that can be integrated with an x-ray fluorescence system and which is capable of being implemented as a fully automated system for in-situ installation and measurements. The pre-concentration cell extracts ultra-trace levels of ionic impurities from aqueous solutions in order to enhance their detection by x-ray fluorescence, and allows for the use of XRF techniques in the sub-part-per-million (sub-ppm) minimum detection level (MDL) region. The pre-concentration cell can be installed on-line for in-situ data collection, analysis, and automatic reporting without human intervention, and because the pre-concentration times are comparatively short, it can be employed in a real time system. The ability to detect such contaminants in real time, and to measure them accurately, is an important improvement over existing techniques. It can also be used for remote sampling, and then transported elsewhere for irradiation and analysis.

This invention is applicable to the detection of a wide variety of ionic contaminants in a wide variety of fluid matrices. For example, this present invention is well-suited for detecting and measuring specific metal contaminants, such as arsenic, in drinking water, and for detecting and measuring other toxic metals such as lead and mercury in industrial discharge streams. It is also useful for detecting and measuring elements in other fluids, such as to ensure that fluids used for various industrial processes are as pure as is needed for those processes, or contain desired elements in desired concentrations.

Figure 1:
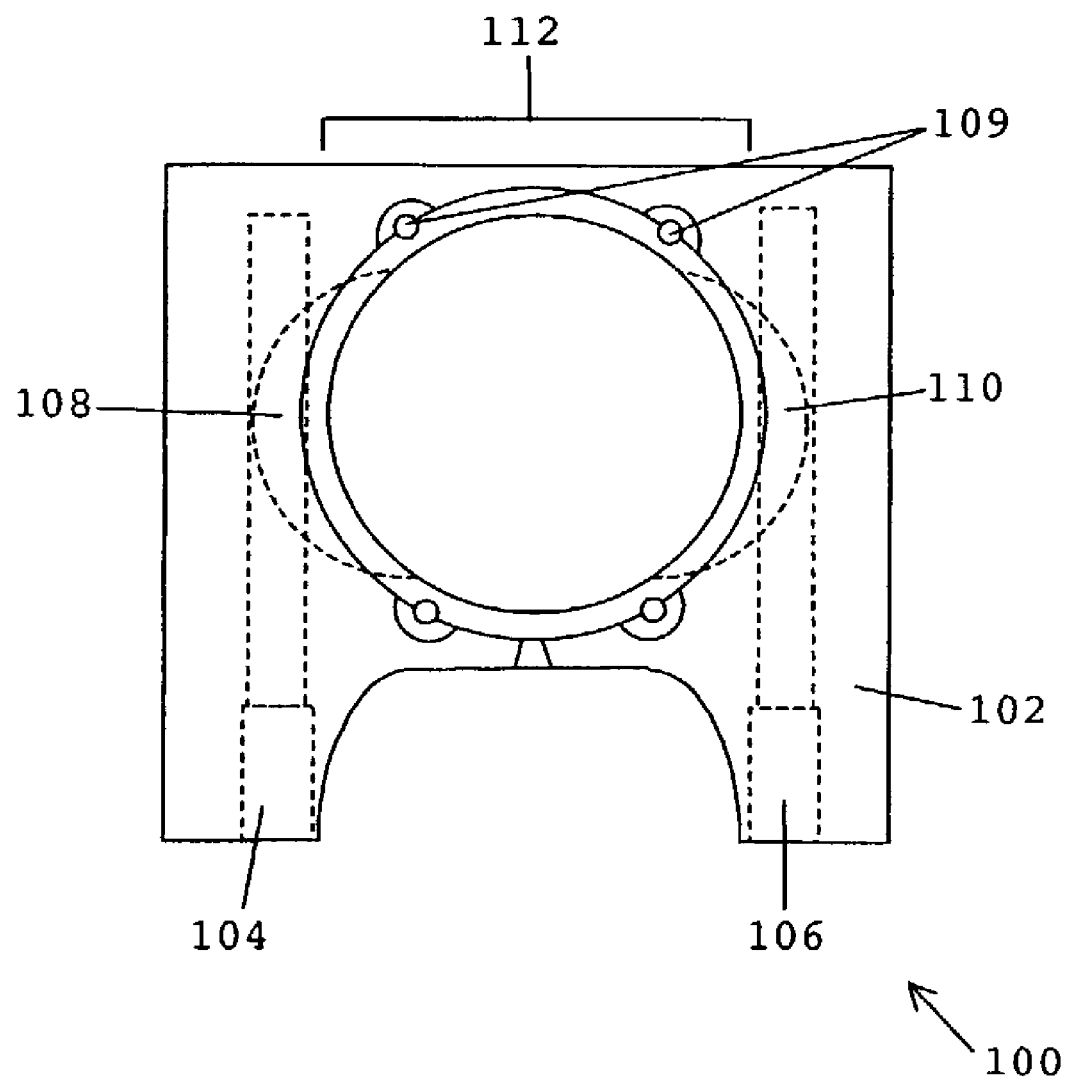
FIG. 1 is a top view of a preferred embodiment of the pre-concentration cell.
Figure 13:
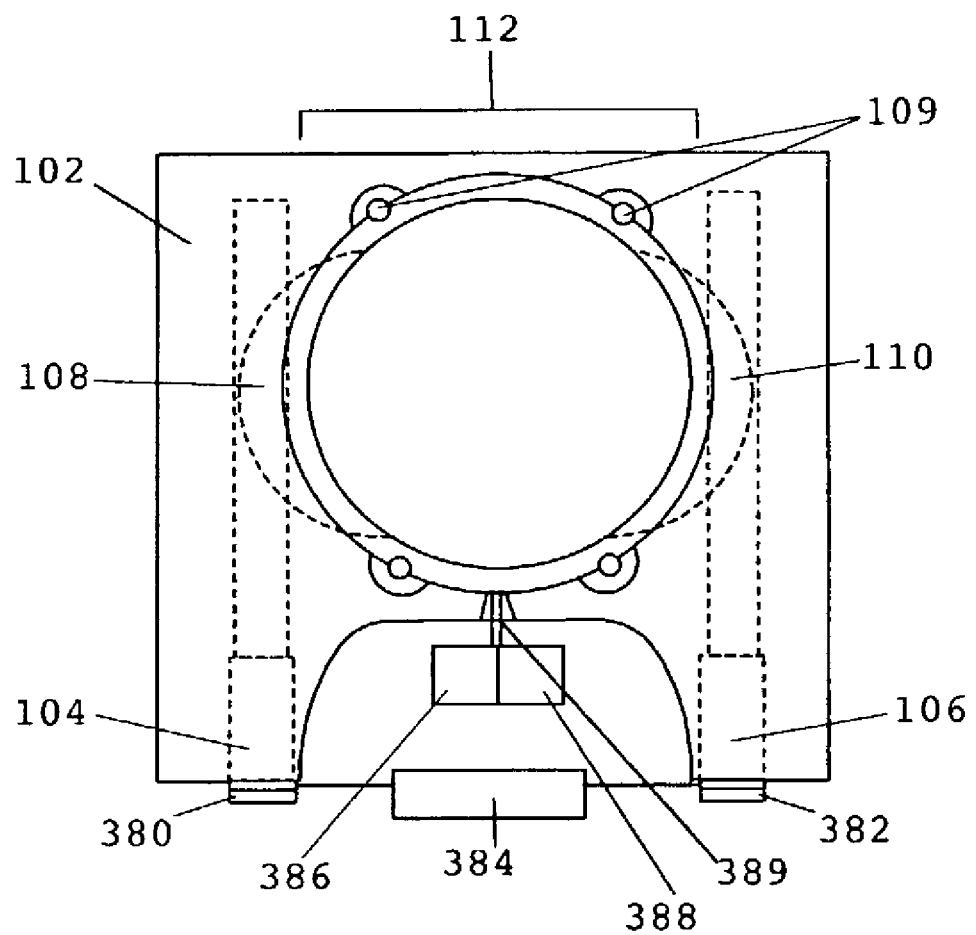
FIG. 13 is a top view of the preferred embodiment of the pre-concentration cell including control modules.
Figure 19:
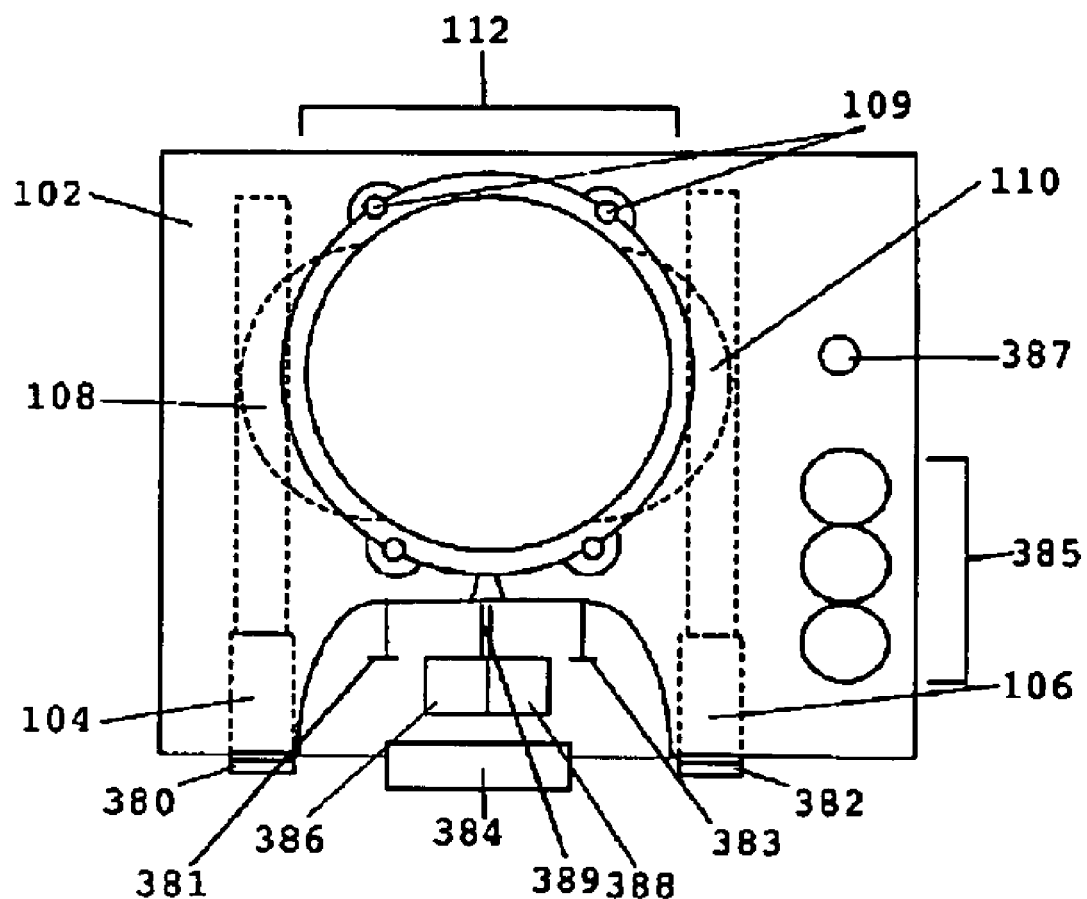
FIG. 19 is a top view of the pre-concentration cell with voltage application means comprising a transportable voltage supply for preconcentration without immediate analysis, enabling subsequent cell transportability to an analysis site.
Figure 21:
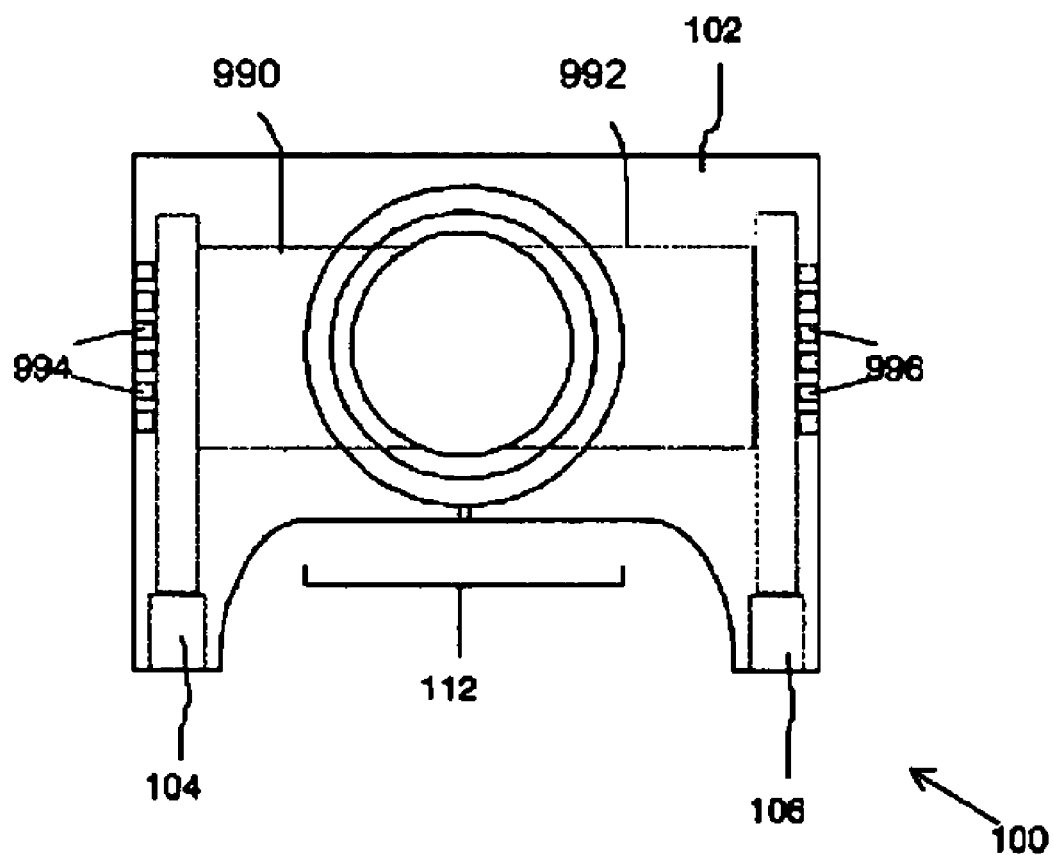
FIG. 21 is a top view of an alternative embodiment of the preconcentration cell.
Figure 22:
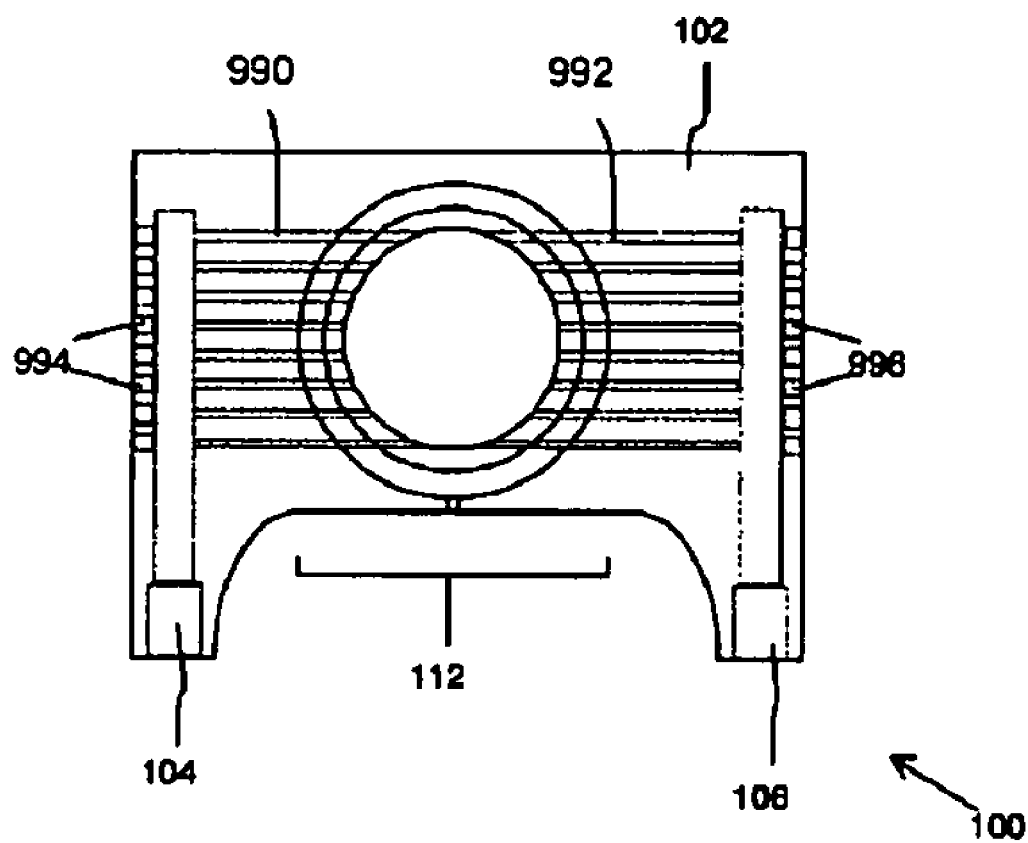
FIG. 22 is a top cross-sectional view of an alternative embodiment of the preconcentration cell with inlet flow tubes.

A primary component of the invention disclosed herein is the ionic pre-concentration cell 100 of FIGS. 1 and 13, (and the very similar transportable pre-concentration cell 101 of FIG. 19). FIGS. 21 and 22 show some alternative cell embodiments. It is well understood that other embodiments are also feasible within the scope of this disclosure and its associated claims. This component will be described in detail in order to better understand the functionality of the in-situ XRF analysis system.

Pre-concentration cell 100 in its various embodiments has the ability to extract ultra-trace levels of ionic contaminants from aqueous solutions. In order to determine the concentration of an impurity in the flow stream, the ratio of the rate of concentration to the flow rate must be maintained constant. Because the rate of concentration is proportional to the concentration of the impurity in the flow stream, maintaining adequate flow rates through the cell 100 ensures that the basic concentration levels in the fluid matrix remain substantially unchanged, resulting in a highly accurate quantitative measurement. This ionic pre-concentration cell 100 provides means of detecting sub ppm levels of dissolved ionic contaminants, a sensitivity not heretofore achievable with XRF and similar analytical techniques outside of a laboratory-based system.

Figure 2:
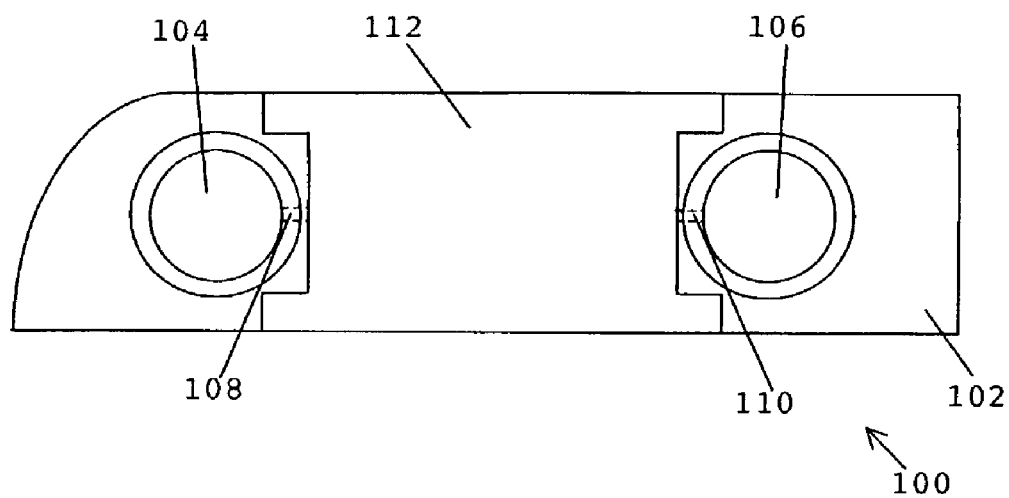
FIG. 2 is a front cross-sectional view of the preferred embodiment of the pre-concentration cell.

As shown in top view FIG. 1 and front view FIG. 2, the ionic pre-concentration cell 100 comprises a cell collector body 702 with an inlet flow port 104, an outlet flow port 106, an inlet flow slot 108, an outlet flow slot 110, an electrode assembly 112 (detailed further in FIGS. 3 and 4), and tightening fasteners 109. Preferably, the cell collector body 102 comprises a non-conductive, low-Z material suitable for use in a high radiation environment. In general, any material is suitable for cell collector body 102 that is non-metallic and non-conductive with the capability or characteristic of being readily machined into shapes. To be avoided are metals such as iron or copper that could leach dissolved ions into the flow stream and thereby cause a false reading (thus the material used must have suitable resistance to ionic leaching). The material must also be resistant to radiation degradation at the x-ray energies to which it will be subjected during testing. Delrin® plastic or any similar material with the aforementioned properties that is known in the art or may become known in the future is suitable for this purpose. Other possibilities include, but are not limited to, other plastics, fiberglass products such as NEMA G-10, or even glass so long as the glass utilized can be properly machined.

The inlet flow port 104 and outlet flow port 106 are preferably passageways laid out substantially parallel to each other and substantially on the same plane on opposite ends of the pre-concentration cell 100. Their illustrated circular cross-sectional shape in FIG. 2 can be varied at will within the scope of this disclosure and its associated claims so long as they permit the aqueous solution being tested to flow therethrough. Between the inlet flow port 104 and the outlet flow port 106, is electrode assembly 112, that connects the flow channel from inlet to outlet of the pre-concentration cell 100, as can be seen by examining FIGS. 1 and 2.

Projecting substantially perpendicularly from inlet flow port 104 to electrode assembly 112 is an inlet flow slot 108 which lies in substantially the same plane as a central flow interelectrode gap 222 (see FIGS. 3 and 4) of electrode assembly 112. Similarly, on the opposite side of the electrode assembly 112, an outlet flow slot 110 connects the central flow interelectrode gap 222 to outlet flow port 106. Outlet flow slot 110 is substantially perpendicular to the outlet flow port 106. These perpendicular configurations of the flow ports 104 and 106 relative to the flow slots 108 and 110 are non-limiting and for illustration only, and other configurations are equally acceptable within the scope of this disclosure and its associated claims.

Figure 3:
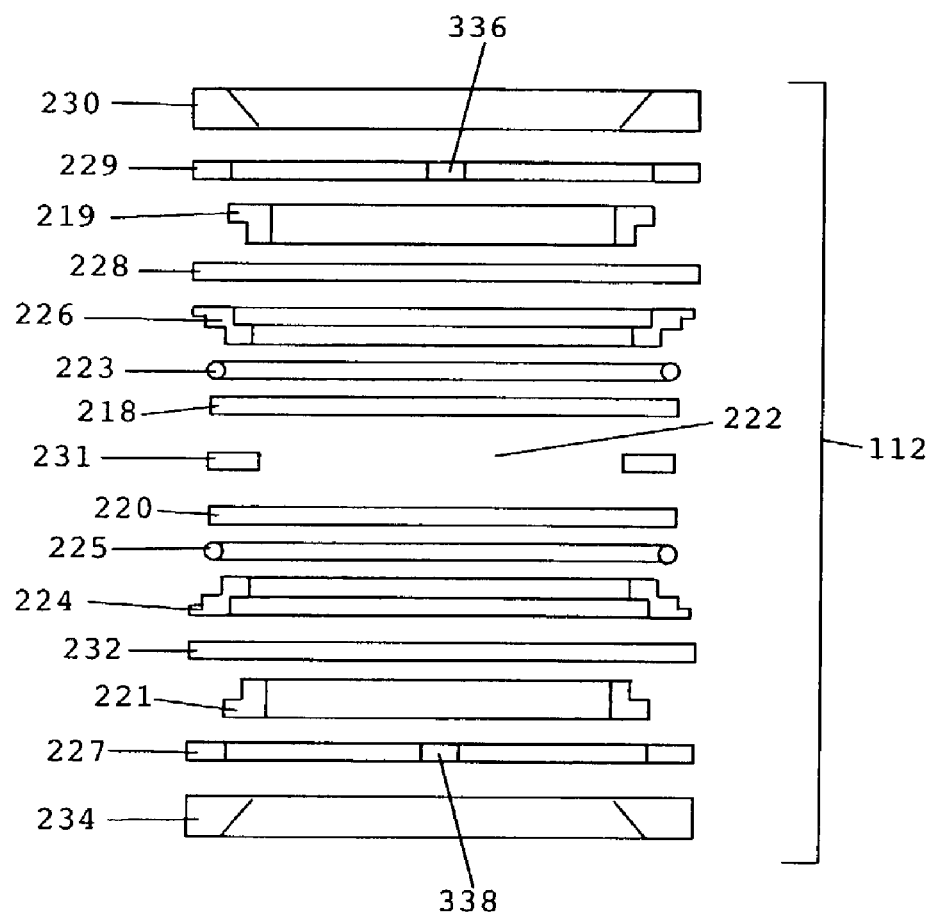
FIG. 3 is an exploded two-dimensional side view of the electrode assembly of the pre-concentration cell.
Figure 4:
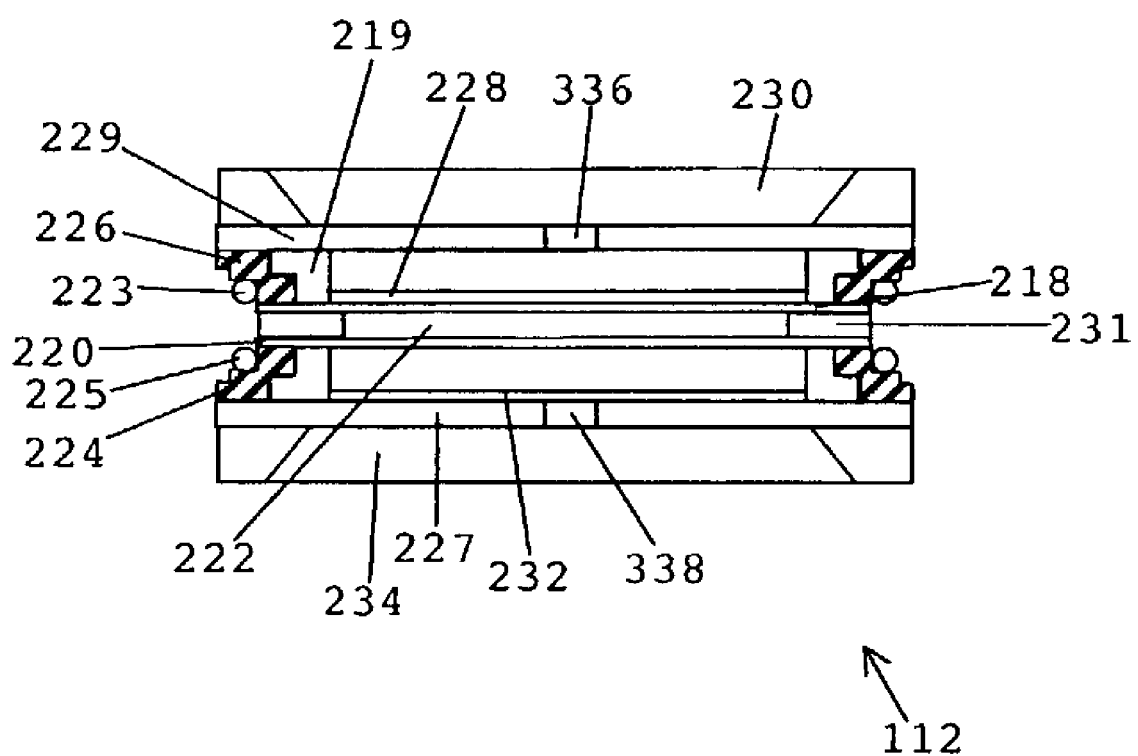
FIG. 4 is a front cross-sectional view of the assembled electrode assembly.
Figure 7:
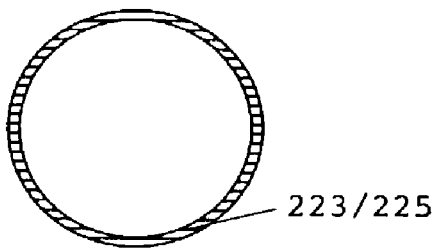
FIG. 7 is a top view of the upper or lower sealing o-ring.
Figure 8:
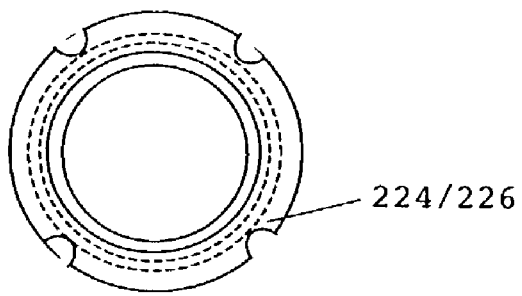
FIG. 8 is a top view of the upper or lower contact ring.

FIGS. 3 and 4 detail electrode assembly 112. High surface area electrodes 218 and 220 separated by central flow interelectrode gap 222, fixed by interelectrode spacer 231 or similar spacing means, comprise an electrical capacitor. Moving outward from central flow interelectrode gap 222, the upper and lower high surface area electrodes (218 and 220) are held in place by upper and lower contact rings 226 and 224, which is sealed by upper and lower sealing o-rings 223 and 225, as shown in a top view in FIGS. 7 and 8, respectively. The contact rings 224 and 226 have essentially a stepped cross-section to hold the electrodes 218 and 220 and windows 228 and 232 in place. The cross-section, as specifically shown in FIG. 3, is a functional design but not in any way a limitation. To minimize noise, contact rings 224 and 226 are preferably fabricated from a low-Z carbon compound or compound with similar electrical and corrosion resistant characteristics.

An upper transmission window 228 highly transparent to the x-ray excitation and fluorescence radiation is held in place, essentially flush with the upper electrode 218 within the contact ring, by an upper window compression ring 219, an upper electrical contact ring 229 and an upper retaining ring 230. Similarly, an optional lower transmission window 232 is held in place by a lower window compression ring 221, a lower electrical contact ring 227, and a lower retaining ring 234. These transmission windows 228 and 232 seal electrode assembly 112 within the pre-concentration cell 100. Voltage is applied to electrodes 218 and 220 via voltage application means for applying a voltage differential. For example, without limitation, voltage is applied to the upper electrode 218 via the upper electrical contact 336 located on the upper electrical contact ring 229. Similarly, voltage is applied to the lower electrode 220 via the lower electrical contact 338 on the lower electrical contact ring 227. Alternatively, but again only as an example without limitation, retaining rings 230 and 234 may themselves double as the electrical contact to the electrodes 218 and 220. Indeed, any suitable voltage application means such as described above or otherwise known or which may become known in the art is acceptable within the scope of this disclosure and its associated claims.

When the liquid under analysis flows through the interelectrode gap 222 with a voltage applied to the electrodes and thereby causing the electrodes to act as a capacitor, oppositely charged ions in the flow stream are attracted to the charged plates where they are trapped in a double layer formation. The amount of charge that the capacitor can hold is proportional to the total surface area of said capacitor. An ideal material for such a capacitor to be used as a preconcentration device for XRF analysis needs to have good conductivity, is porous with optimum pore sizes (large enough to facilitate ion transport in and out of the material and small enough to have a very high internal surface to void ratio), and is made of the lowest atomic number material possible (to be as transparent as possible to x-rays).

Nanocellular carbon (NCC), manufactured by Ocellus Inc. of Livermore, Calif., which is disclosed in U.S. Pat. No. 5,945,084, is an ideal material for this purpose, though it is understood that other materials with similar properties that might be developed in the future may also be suitable as well within the scope of this disclosure and its associated claims. NCC comprises conductive sheets of carbon with very high surface to volume ratio by incorporating a distribution of pore sizes narrowly grouped around a well-controlled optimum size. The optimum pore size is selected to enable ions to readily migrate into the pores for double layer formation and out again for cleaning upon removal of the voltage.

While the aerogel employed by Farmer could also be used for pre-concentration in accordance with this invention, it is less preferred, since it has significantly more smaller pores that are too small to establish formation of double layers and inhibit the transport of the ions to and from the electrode surfaces. Trapped ions that are not removed during the self-cleaning cycle adds to a cumulative background and decrease the sensitivity of the XRF analysis over time.

Thus, for the concentration of dissolved ions to facilitate detection that is of interest here, the high surface area electrodes 218 and 220 preferably comprise NCC or any similar material that may be developed in the future in which the size of the pores can be optimized for double layer formation and for transport of the ions, and less preferably, but still within the scope of the invention, a carbon aerogel. For formation of double layers and ease of ion transport in and out of the pores, the characteristic dimension of the pores should be in the 20±10 nm range. NCC with properties similar to what is disclosed within U.S. Pat. No. 5,945,084 is preferred because it can be manufactured with a higher proportion of its pore sizes engineered to achieve high surface area with average pore size clustered around the desired value to provide greater collection capability for the desired ions, and for ease of cleansing.

The specific properties of this NCC electrode material which make it suitable for this application include a large plurality of pores characterized by a specific surface area of at least approximately 100 $m^2/g$; an average pore diameter of said pores between approximately 30 nm and 10 nm per pore; a distribution of pore diameters grouped with a standard deviation of less than approximately 10 nm around the average pore diameter; an x-ray transparency greater than approximately 90% for characteristic photon energies from an element of interest for which a fluidic concentration is to be measured by said system; electrical conductivity of 10–40 mOhms-cm when fabricated into a ¼ mm thick electrode; the ability to contain approximately at least 0.1% by weight of foreign material relative to the high surface area material prior to saturation; high structural rigidity wherein a displacement under the flow of the fluid does not exceed approximately 0.25 mm; high wetting ability wherein an approximately ¼ mm thick sheet of the high surface area material becomes substantially wetted in less than approximately three seconds; and freedom from metallic impurities in excess of approximately 0.5 parts per million, when measured by XRF analysis. In order to achieve satisfactory performance, the use of any alternative or substitute material for the upper and lower high surface area electrodes 218 and 220 possessing similar properties to those outlined above is regarded to be within the scope of this disclosure and its associated claims.

Figure 5:
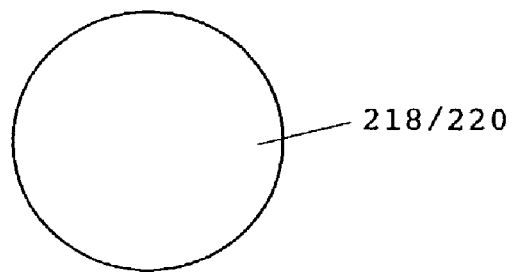
FIG. 5 is a top view of the upper or lower high surface area electrode.
Figure 6:
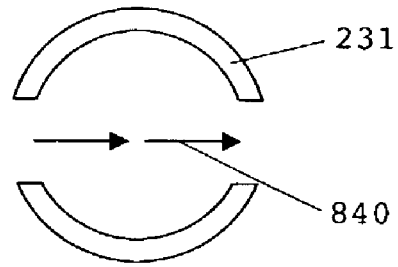
FIG. 6 is a top view of the interelectrode spacer.

FIG. 5 is a top view of the upper and lower high surface area electrodes 218 and 220. As shown in the figure, they are typically round in shape but could be formed in any alternative shape within the scope of this disclosure and its associated claims. Upper and lower high surface area electrodes 218 and 220, again, preferably comprise the NCC materials such as disclosed in U.S. Pat. No. 5,945,084. The thicknesses of the high surface area electrodes 218 and 220 are determined by the transmission probability of the x-ray radiation to be used for analysis. For example, assuming that water is the liquid to be analyzed, then: if the radiation being analyzed is 15 keV (typical of K-line radiation in the region of atomic number 39 or L-line radiation in the region of atomic number 95), the electrode material should be about 8±2 mm thick; 10 keV radiation (typical of K-line radiation in the region of atomic number 32 or L-line radiation in the region of atomic number 80) would require 2.5±1 mm optimum thickness; while x-rays at or below 5 keV (typical of K-line radiation in the region of atomic number 23 or below or L-line radiation in the region of atomic number 59 or below) could only effectively transit less than ½ mm of electrode plus matrix (again assuming water for the matrix to be analyzed).

More generally, when an x-ray passes through matter, its intensity is attenuated exponentially as a function of the distance characterized by the mass absorption coefficient of the matter, $\mu$ (in cm$^2$/gm), which is a function of the photon energy and the atomic number of the material, see, for example, the Center for X-ray Optics X-Ray Data Booklet PUB-490, Douglas Vaughan ed. Lawrence Berkeley Laboratory, October 1985, pages 2–28 through 2–48. In general, the lower the energy of the photon, and the higher the atomic number of the material, the larger is the value of the mass absorption coefficient. The numerical inverse of the product of the mass absorption coefficient ($\mu$, in cm$^2$/gm) and the density of the material ($\rho$, in grams/cm$^3$) is given by (cm)=$1/\mu$ $\rho$, and is the optical depth of the photon in the material, that is, the path length of material of density $\rho$ with mass absorption coefficient $\mu$ that will absorb 1/e or about 63% of the incident photons. Because of the attenuation effect, most of the fluorescence photon signals detected will have originated from the layer of the electrode on the order of the optical depth closest to the detector. Any additional materials present will contribute more significantly to the background than the signal. For this reason, to obtain maximum sensitivity, the thickness of the electrode nearer to the x-ray source and fluorescence detector should not exceed the optical depth of the photon to be detected, that is, this thickness should less than or equal to The two electrodes need to be matched (to ±10% or so) in order to maintain the desired electrical properties.

Thus, for example, for detection of arsenic, which has an x-ray energy at about 10 keV, the NCC electrode thickness can be as much as 1 mm, and even up to 2 mm. However, for detection of the lighter elements (Z<20) for which the fluoresce photon energy is only a few keV, the electrode thickness should optimally be around 100 micron.

From the same signal to background noise consideration, the central flow interelectrode gap spacing 222 (predetermined interelectrode gap width) between electrodes 218 and 220 should be made very small to limit the amount of fluid entrained between them, without excessively impeding the flow of the sample fluid through the cell. Excessive flow impedance would require a high pressure to induce the flow which would cause the thin window that is part of the system (described below) to bow out, and that would have detrimental effects. In special cases the Venturi effect could be utilized to balance the pressure required against the desired flow rate, however, this would limit the particular design to a limited range of flow rates depending upon the viscosity of the liquids being analyzed. Typically, a characteristic interelectrode gap spacing of approximately 2 mm is preferred. Minimum values range as low as 1 mm, 0.5 mm, and even 0.25 mm. Maximum values range as high as 2 mm, 5 mm and even 10 mm. The quantitative determination of an optimum width for the interelectrode gap is discussed in further detail later on.

Figure 9:
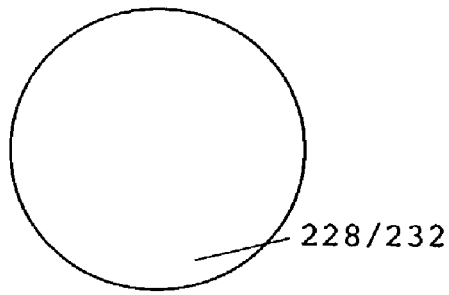
FIG. 9 is a top view of the upper or lower transmission window.
Figure 10:
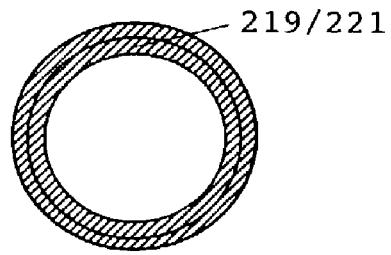
FIG. 10 is a top view of the upper or lower window compression ring.
Figure 11:
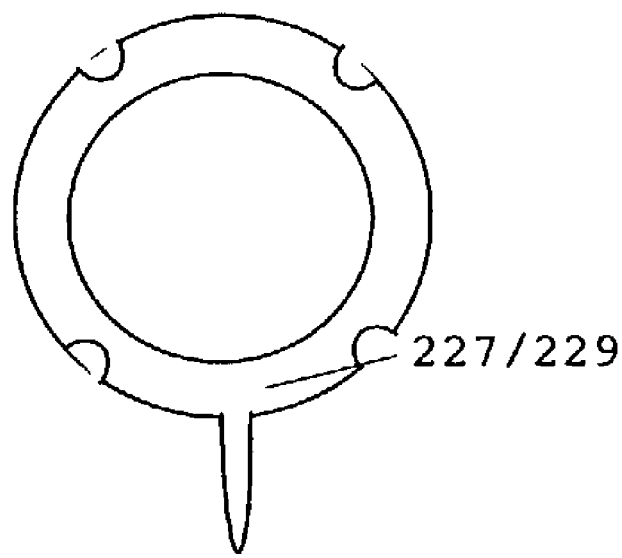
FIG. 11 is a top view of the upper or lower electrical contact ring.
Figure 12:
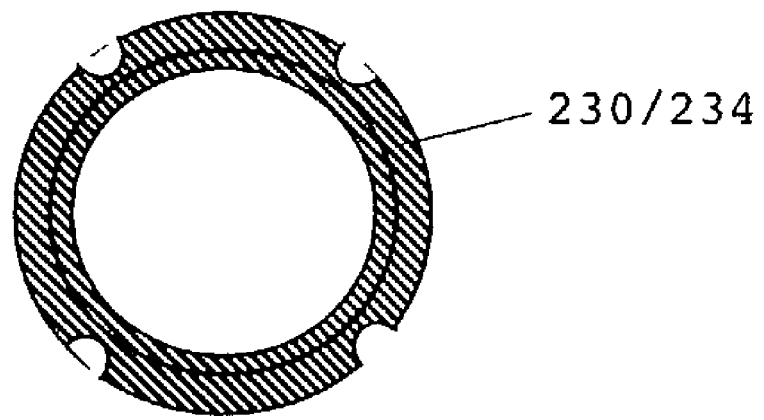
FIG. 12 is a top view of the upper or lower retaining ring.

A top view of the upper and (optional) lower transmission windows 228 and 232 is shown in FIG. 9. The transmission window is preferably round (but it, and all the other components in FIGS. 5–11, can be any suitable shape within the scope of the disclosure and claims) and is fitted to integrate with the contact rings 224 and 226 and the window compression rings 219 and 221. FIG. 10 is a top view showing the details of the upper and lower window compression rings 219 and 227. As shown in these figures, the L-shaped ringed structure has a central opening to allow access to the transmission windows 228 and 232 while firmly holding them in place around their perimeter. FIG. 11 shows a top view of the electrical contact rings 227 and 229 and FIG. 12 shows a top view of the retaining rings 230 and 234. These rings are sized to include pass throughs to allow access to the transmission windows 228 and 232 and comprise indentations to allow for use of the tightening screws 109.

Upper and lower thin transmission windows 228 and 232 serve dual purposes by enabling the excitation x-ray and fluoresce photons to pass therethrough with minimum attenuation and also by acting as a fluid barrier to seal pre-concentration cell 100. Preferably, transmission windows 228 and 232 comprise Kapton®, a patented proprietary material manufactured by DuPont Chemicals. Kapton®, is a hydrocarbon-based rigid plastic material that is ideal for x-ray radiation transmission (it is typically more transparent and scatters less radiation than most fluids of interest for analysis, by a factor of about ten) and its mechanical properties minimize window bowing (bending) so that less than a tenth of the thickness of liquid being analyzed is entrained between the window and the electrode. Such bowing would be undesirable in this application because it would lead to fluid entraining between the bent window and the electrode that would then contribute to the attenuation of the X-ray and add to the background noise signals.

Any suitable material can be utilized for the x-ray transmission window as long as it is compatible with the fluid being analyzed, transmits x rays of interest efficiently (high signal), minimizes scattering of x rays that are not of interest (low noise), and is rigid enough, even as a thin window, to resist bending and thus remain in intimate contact with the high surface area electrodes 218 and 220 under any flow rates and pressures that might be used. Kapton is preferred for its mechanical stiffness compared to other suitable materials such as polyproylene, Saran, Formvar, Mylar, or Kimfoil, but it is understood that the use of these latter and similar materials also falls within the scope of this disclosure and its associated claims. Kapton is also preferred because it is low in contaminants as compared to Beryllium and compatible with a wide variety of fluids as compared to Boron Nitride. But, it is to be understood that other materials such as Beryllium and Boron Nitride could be used in place of Kapton if future advances in materials technology should manage to overcome these problems and if these materials can be fabricated as thin windows providing a water barrier with suitable x-ray transparency, corrosion resistance, and resistance to bowing.

As a more general rule, any material known or which may become known in the art is acceptable to be used for window 228 and optionally window 232, so long as that material comprises: an atomic number below 10; structural rigidity to support up to 1/10 atm. of pressure without bowing more than approximately 100 microns; substantial impermeability relative to said fluid; x-ray transparency greater than 90% for characteristic photon energies from an element of interest for which a fluidic concentration is to be measured by said system; x-ray scattering therefrom minimized to less than approximately 10% of radiation scattered from a column of said fluid equal to one optical depth in said fluid of a characteristic photonic energy from an element of interest for which a fluidic concentration is to be measured by said system; and freedom from any single contaminant in excess of 1 part per million, when measured by x-ray fluorescence.

Further, and also importantly, the Kapton or similar-material thin window is configured to be in intimate contact with the high surface area electrode. "Intimate contact," as used herein, is functionally defined to mean that the thin window is close enough to the high surface area electrode, and remains close enough to the high surface area electrode even under pressure from the flow of the fluid matrix under analysis, such that the absorption and scattering due to intervening entrained fluid between thin window and the high surface area electrode is less than approximately the absorption and scattering due to the window material itself.

The thickness of the window should be significantly less than the attenuation length for the energy of the x-ray yet thick enough to support the water pressure. For x-ray energies in the 1 to 10 KeV range for measurement of light elements, a preferred thickness for the thin Kapton windows is approximately 8 microns, to maintain maximum sensitivity for the measurement of light elements. For measurements of heavier elements, the x-ray energy needs to be higher in the 10–20 keV range and a thicker window (8–25 microns) may be used to allow for higher pressure to increase the flow rate.

The cross-section of the pre-concentration cell 100 shown in FIG. 4 and the exploded view in FIG. 3, detail the layout of the electrode assembly 112 within the pre-concentration cell 700. Although the pre-concentration cell 100 is presented as a horizontal assembly throughout this disclosure, it is to be understood that it is orientation independent, such that it can be implemented in any configuration, such as horizontal or vertical, or anything in between, that fits best with the application. It is further observed that the terms "upper" and "lower" are used to refer to such elements of preconcentration cell 100 as the electrodes 218, 220 and the windows 228, 232. These terms are to be understood not in terms of "higher" or "lower" with respect to a gravitational field, but in terms of how preconcentration cell 100 is to be oriented relative to the x-ray source means 644 and fluorescence detector 648 for XRF analysis. The "upper" pre-concentration cell elements are to be understood as those that ultimately are to face the x-ray source means 644 and x-ray fluorescence detector 648 during the XRF analysis, and that the "lower" elements are those on the far side of this x-ray equipment. If the x-ray equipment were to be placed gravitationally below the cell, then the "upper" elements would be gravitationally lower than the "lower" elements.

It is also to be noted that the various window properties discussed above are optional for the "lower" window, insofar as it is possible to simply seal the "lower" face of the preconcentration cell with any material that provides a suitable fluid barrier and will not degrade under x-ray exposure or contact with the fluid of interest. The x-ray scattering and transmission properties of the lower face of the cell are of much less importance than those of the "upper" window since it is the upper window through which the x-rays are transmitted and XRF readings are taken.

FIG. 13 shows a top view of the preferred embodiment of the pre-concentration cell 100 including the necessary control modules. To enable automated operation of the system, the preconcentration cell is fitted with an inlet automated valve 380 connected to the inlet flow port 104 and an outlet automated valve 382 connected to the outlet flow port 106. Such valves are capable of being remotely controlled to turn on and off the flow stream into the pre-concentration cell. In addition, and desirably, ionic pre-concentration cell 100 comprises a variety of diagnostics to set, monitor and control system performance, such as, but not limited to: flow control means 384 comprising, for example, not limitation, a pressure sensor to set the flow potential and flow meter to monitor the flow rate; voltage application means 389 comprising, for example, not limitation, an electric potential and current meter 386 to set and monitor the applied potential (voltage differential); and leakage current monitoring means 388 to monitor the leakage current which gives a measure of the conductivity of the sample fluid due to presence of dissolved ions and the rate that they are being extracted from the flow stream.

Figure 14:
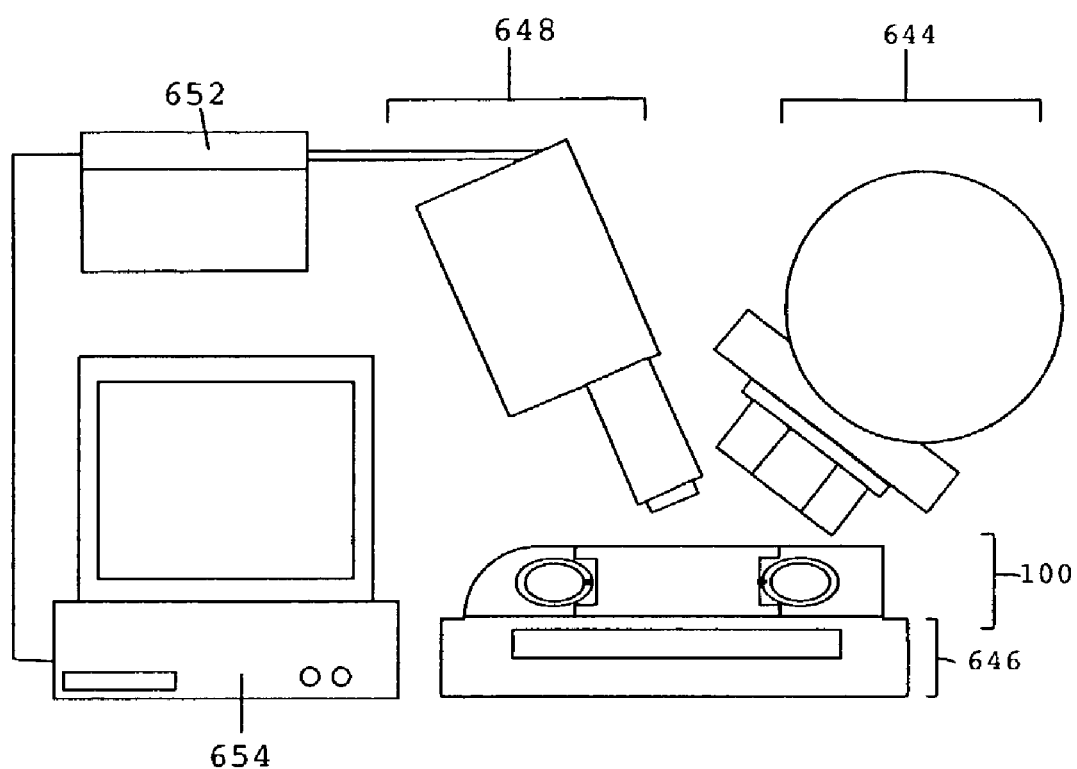
FIG. 14 is a schematic view of the overall XRF detection and analysis device, system and method.

The pre-concentration cell 100, as described above, is an enabling component to facilitate automated detection and measurement of impurities in fluids at sub-ppm concentration level as shown in FIG. 14. For purpose of illustration, the size of the pre-concentration cell is greatly exaggerated. As shown in FIG. 14, an x-ray source means 644 for providing energy for fluorescing the captured ions in pre-concentration cell 100 is situated at an angle above pre-concentration cell 100. X-ray source means 644 may also comprise an x-ray emitting, sealed radioactive source. As is common practice in XRF systems, a filter ladder (not shown) may also be included between the X-ray source and the pre-concentration cell. The filter ladder holds filters of different material and thickness to shape the spectrum of the excitation X-ray from the source.

A beam stop assembly means 646 for confining the radiation to the pre-concentration cell 100 and preventing radiation leakage to the outside is placed opposite the x-ray source in the pre-concentration cell 100 lower window area. The beam stop assembly preferably comprises three elements, namely, silicon, copper and tin, with the silicon layer closest to the source/detector area and the tin layer furthest away. All beam stop assemblies known or which may become known in the art are considered as possible for use here.

Detector means 648 for collecting the fluorescence produced by the captured ions in pre-concentration cell 700 (i.e., for detecting photons emitted from preconcentration cell after it is irradiated) is positioned on the same side of the pre-concentration cell 100 as the the x-ray source 644 and is oriented for such collection. This arrangement is for purpose of illustration as one possible implementation. Any other arrangement that directs the x-ray to the pre-concentration cell and allows the fluoresce photons to be collected by the detector are also within the scope of this invention as disclosed and claimed.

Analysis means 652, 654 for analyzing this fluorescence data, such as but not limited to the illustrated multi-channel analyzer and host computer, is used for processing and analyzing the fluorescence image data captured by x-ray fluorescence detector 648. The host computer illustrated by 654 can optionally be multi-functioned to control the operation of the system and for data analysis.

The present invention utilizes as x-ray source means 644, preferably, but without limitation, a Kevex model 5039S X-ray source which generates up to 50 keV electrons at 1.0 mA. The resulting Bremstrahlung radiation from a tungsten target generates the primary x-ray beam from the source. The input x-ray flux must have sufficient energy and intensity to excite the metal ions captured in the pre-concentration cell 100 to fluoresce in order for detection to take place. Alternatively, the present invention could also utilize as x-ray source means 644, a sealed x-ray source, obtainable from vendors such as Isotope Sciences of Canoga Park, Calif. The advantage of sealed sources is that they do not require power inputs from external sources. Similarly, any other type of x-ray source means 644 known in the art or which may become known in the art, which meets the functional requirements specified herein, is also suitable for use within the scope of this disclosure and its associated claims.

The preferred, but without limitation, x-ray fluorescence detector means 648 is an Amptek model XR-100CR solid state x-ray detector with 5 mm crystal in combination with a multi channel analyzer (MCA8000) also from Amptek. This system is either battery powered or powered from conventional power sources. X-ray fluorescence detector means 648 may also comprise any other suitable detectors known or which may become known in the art, within the scope of this disclosure and its associated claims. A combined x-ray source and a detector as a single unit can also be used in conjunction with the concentration cell installed in the flow stream as a complete system for detection of impurity concentration in flow streams.

For fully automated operation, the system needs to be connected to a computer, such as a personal computer (PC). This can be separate from host computer illustrated as 654, or as noted above, can be a function provided by the host computer. The function of the computer is to control the operation of the system; to collect, store and analyze the data; and if desired, to transmit the data via a modem, wireless, or similar telecommunications means.

The functions required to control the operation of the computer may include but are not limited to operations which: turn on and off the valves to allow the sample flow stream through the system; set the pressure on the flow pressure regulator; monitor the outputs from the flow meter and regulate the flow pressure to maintain constant flow; set and apply a voltage to the electrodes; monitor and store the leakage current across the capacitor; turn on and off the XRF source if a non-radioactive source is used and set the voltage applied; turn on and off the multi-channel analyzer and record the output spectrum of the analyzer at frequent intervals; and accept inputs from an operator to set and store the desired operating parameters.

The functions required to analyze the data may include but not be limited to: analysis of the stored data to determine the count rate in each energy channel; detection of signals above background; and comparison of detected signals with a stored lookup table to identify the elements, using a variety of commercially available or custom-developed algorithms.

The functions required for transmission of data may include but are not limited to connecting to a modem or transmitter or other telecommunications means at user specified-times or intervals, or to send a signal or trigger and alarm when the concentration of any specified impurities identified exceeds preset threshold values; and calling up the data and transmitting the data. Alternatively, all or some of these functions noted in this paragraph may be performed by human intervention.

Figure 15:
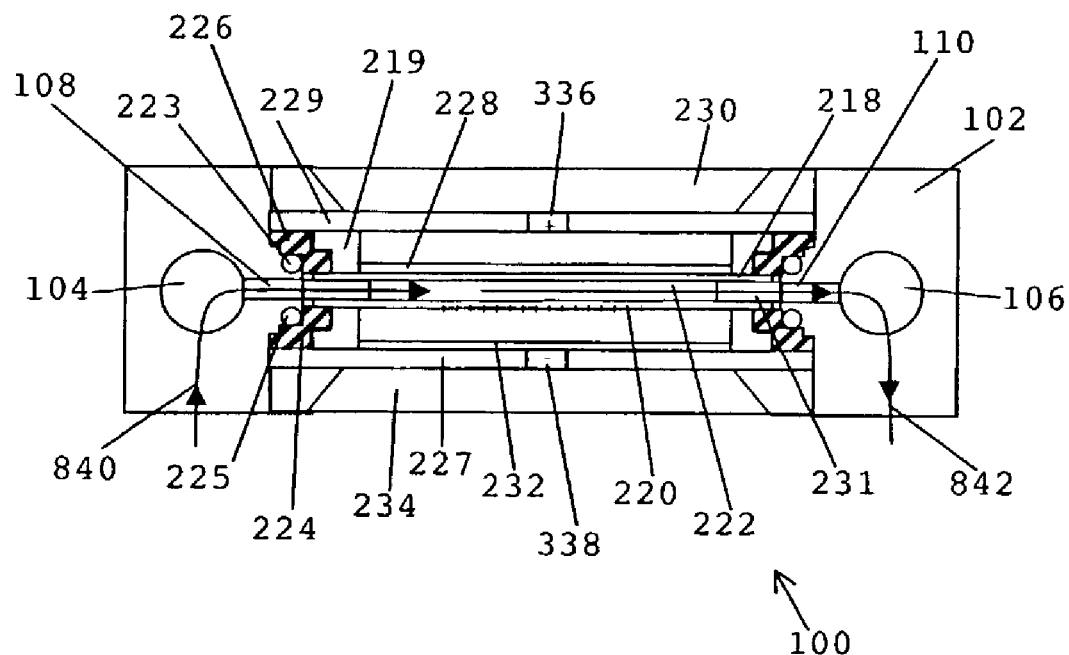
FIG. 15 is a front cross-sectional view of the operation of the pre-concentration cell.

Referring to FIG. 15, the operation of the XRF analysis system will now be described. Because an x-ray of sufficient energy is capable of inducing fluorescence in all elements, the materials comprising the cell itself will contribute to the signals detected. Therefore, prior to its use, each pre-concentration cell must be characterized to establish the background that it contributes, as well as its other pertinent characteristics. Each cell thus comprises background data, sensitivity data, and ion extraction rate data acquired from and associated therewith, which is measured after the cell is fabricated and assembled following the manufacturing process. This establishes a calibration for the cell.

To characterize the background data associated with the pre-concentration cell, the flow channel volume 222 is first filled with distilled water of high purity (or any other fluid to be analyzed, in a highly pure form). The distilled water is introduced through the inlet valve 380 of inlet flow port 104 until the cell is full of water. Then, the outlet valve 382 of outlet flow port 106 is shut off in order to trap the water in the cell body 100. The X-ray source 644 and the multi-channel analyzer 652 and detector 648 are then turned on when the cell is completely filled to record the signals received. The signals are photons of different energies arriving at the detector 648. The multi-channel analyzer 652 resolves the arriving photons into discreet energy channels according to their energy, to output a spectrum of intensities proportional to the number of photons in each energy channel detected. As the photons continue to arrive, the intensity in each energy channel will grow as a function of time.

This intensity spectrum consists of both a continuum due to scattering of the primary x-ray to different energies, and discreet bands due to photons from x-ray fluorescence with energies characteristic of each element of the cell. The quantity of interest is the rate of growth of the intensity of each energy channel, which represents the rate that the fluorescence photons are generated and is a measure of the concentration of that particular element present. By sampling the intensity spectrum at frequent intervals, it is possible to obtain a plot of the intensity in a particular energy channel of interest as a function of time. The data points can be fitted by an analytical function by various mathematical techniques such as by least-mean-square method. The first derivative of this function is the rate at which photons of the particular energy are detected, which gives a relative measure of the concentration of a particular element in the cell.

Because the elements present in the cell are fixed, the rate of photons emitted, on average statistically, is constant. Therefore, if all operating parameters are maintained constant, the intensity of photons detected in each energy channel is expected to be a linear function of time, and its first derivative would be a constant. Determination of the rate of detection of photons in specific energy channels of interest establishes the background characteristics of the preconcentration cell.

In sum, this background data comprises data related to a rate at which photons are detected to be emitted from at least one background data energy channel of the preconcentration cell when the cell is filled with a highly purified form of a fluid of interest and exposed to x-rays.

Once the background is established, the concentration of impurities in any flow stream can be determined by observing the rate of increase of photons detected as the impurity ions are captured in the double layer when a voltage is applied to the electrode. However, in order to obtain quantitative measurement of the concentration of each element present, two additional calibration steps are needed. The first is to determine the sensitivity of the system in terms of relating the photon detection rate to the number of impurity elements present (sensitivity data). The second is to relate the rate at which the impurity elements are captured in the double layer to the concentration in the flow stream (ion extraction rate data). Both calibration steps are also part of the data associated with each concentration cell, and are also established following the manufacturing process.

The sensitivity data is obtained by replacing the distilled water of high purity with a first calibration solution containing known concentrations of one or more impurity ions of interest at levels above the minimum detection levels of the x-ray system. The procedure for establishing the background is then repeated. Because the concentrations of the specific impurities are above the MDL, the intensity of photons corresponding to their characteristic energy will grow at a faster rate then in the previous case. However, because their concentration is constant, the rate of growth will also be constant. Using the same procedure as before, it is then possible to obtain a rate of growth of the intensity. After subtracting out the growth rate due to the background, the result is the growth rate due to the presence of the impurities in the calibration fluid. Since the concentration of the impurity in the calibration fluid is known, it is now possible to quantitatively relate the growth rate to the impurity concentration quantitatively.

In sum, this sensitivity data comprises data related to a rate at which photons are detected to be emitted from at least one sensitivity data energy channel of the preconcentration cell when the preconcentration cell is filled with a first calibration solution containing at least one element of interest in the fluid of interest in known concentration above a minimum detection level of the system and exposed to x-ray.

The final calibration step is to relate the growth rate to the concentration in the flow stream, to obtain ion extraction rate data. For this step, the first calibration solution containing known impurities with concentration above MDL is purged from the system and a second calibration solution is spiked with one or more impurities of interest at known concentration levels below the minimum detection levels of the system. The impurities are introduced into pre-concentration cell 100 under regulated pressure to maintain constant flow rate and are shown as input fluid flow 840 in FIG. 15. Input fluid flow 840 is introduced to the pre-concentration cell 100 via the inlet flow port 104 and the inlet flow slot or tube array (for the tube array, see FIG. 20 discussed below). The input fluid flow 840 continues through the central flow interelectrode gap 222 of the electrode assembly 172, and is exposed to a predetermined voltage applied across the upper and lower high surface area electrodes 218 and 220, respectively, via the upper and lower electrical contacts 336 and 338, respectively. Importantly, this predetermined voltage is set below the electrochemical potential of the impurity ion species in the calibration fluid as well as the potential that can lead to electrolysis of water so as to avoid any permanent changes in the background readings as a result of performing measurements.

Figure 16:
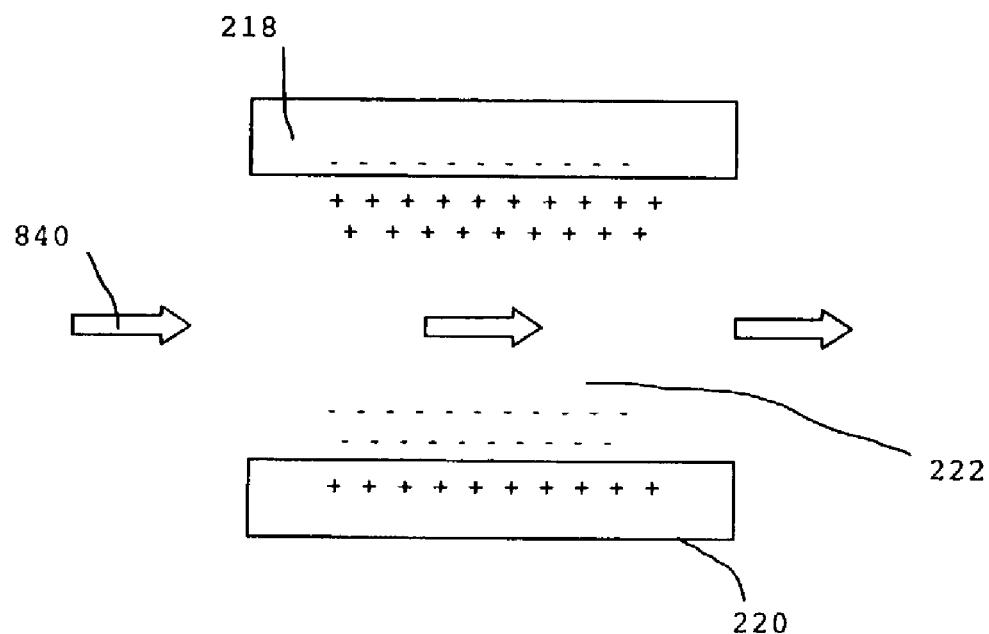
FIG. 16 is a schematic view illustrating the double layer formation in the ionic pre-concentration cell.

The presence of the applied voltage will cause the ions in the flow stream to migrate towards the oppositely charged electrode. The rate of migration of each ionic species is determined by its electric mobility in the fluid. As the ions reach the electrode, they are captured in the double layer, gradually building up their concentrations on the surface of the electrodes. During this time, the spectrum of photons cumulatively detected are continuously recorded at frequent intervals. The double layer formed between the upper electrode 218 and lower electrode 220 is detailed in FIG. 16. The figure shows an exploded view of the interelectrode gap 222, the flow stream 840 through it, and the ion migration during the double layer formation.

The intensities of photons in the energy channels corresponding to the characteristic energy of the impurities in the calibration fluid is sampled at frequent intervals to determine their rates of growth. As long as the concentration of the impurity in the double layer is below the detection level of the instrument, the rate of growth will remain the same as for the background case and its intensity will remain as a liner function of time. With continued accumulation, however, the concentration will eventually exceed the minimum detection limit for the impurity. As a result, the intensity as a function of time will gradually deviate from being linear and the first derivative of this function will no longer be a constant, since the rate of detection is increasing. The second derivative of this function now provides the rate that the impurity ions are being captured in the double layer. Using the scaling factor that relates the count rate to the impurity concentration established for the cell, the rate can be related to the number of impurity ions being captured by the double layer. Since the concentration of the impurity in the flow stream is known, a second scaling factor that relates the growth rate to the concentration is established.

In sum, this ion extraction rate data (scaling factor) comprises data related to a rate at which photons are detected to be emitted from the at least one ion extraction rate data energy channel of the preconcentration cell when a second calibration solution containing the at least one element of interest in the fluid of interest in known concentration below the minimum detection level of the system is flowed through the central flow interelectrode gap at a substantially constant flow rate while the voltage application means applies the voltage differential across the electrodes below an electrochemical potential of the at least one element of interest and below an electrolysis potential of the second calibration solution, and is exposed to x-rays.

For accurate determination of impurity concentrations in a flow stream, the pre-concentration cell must be calibrated with background data, sensitivity data, and ion extraction rate data for each impurity of interest to be measured. While the same cell can be calibrated for all detectable elements (all impurities of interest), that cell can be used only for measuring the concentration of elements for which that cell has been calibrated. All of the calibration procedures, however, can be fully automated. Once the background and the scaling that relates the count rate to the number of impurity ions in the double layer, and the growth rate of the fluorescence photons detected to the concentration of the impurity ion in the flow stream are established following the manufacturing process, the system is ready for general application to measure (test) impurity concentrations in sample flow streams.

It is to be understood that the calibration data comprising the background data, sensitivity data, and ion extraction rate data described above is a preferred example of the type of data that lays the foundation for measuring concentrations of elements in the fluid, but that a person of ordinary skill may find other ways of establishing this data foundation in a manner that is similarly well-suited to measuring concentrations of elements in the fluid, and that is regarded to fall within the scope of this disclosure and its associated claims. Thus, in more general terms, irrespective of the specific form of this data foundation, each preconcentration cell comprises data associated with said cell enabling a concentration of at least one element in said fluid to be deduced, and the disclosed method for detecting and measuring concentrations of elements in fluids comprises deducing a concentration of at least one element in said fluid, using data associated with said cell.

The procedure for measuring impurity concentrations (accumulating test data) in any sample flow stream is the same as the (final, ion extraction rate data) calibration procedure for relating the growth of the count rate to the impurity in the calibration fluid spiked with a low concentration of the impurity of interest. Continuing with the description of FIG. 15, an electrostatic potential (voltage differential) applied to the upper and lower high surface area electrodes 218 and 220 and across the fluid flow 840 through central flow interelectrode gap 222 establishes a current of migrating ions from the fluid flow. For a specific gap 222 and a fixed applied voltage between the upper and lower high surface area electrodes 218 and 220, the current will self-adjust to match the conductivity of the sample to be analyzed.

Since the concentration of an impurity in the flow stream is determined by measuring the rate at which the impurity ions are captured in the double layer, it is essential that the concentration in the flow stream remain relatively constant. Therefore, unlike the design for a deionization cell where the objective is to maximally extract the dissolved ions from the flow stream, the operation of this pre-concentration cell requires that only a small percentage of each impurity species present be extracted, preferably not more than a 1% extraction percentage, with 2%, 3%, 4% and at most 5% being possible, but successively-less desirable options. This is accomplished by adjusting the flow rate to assure there is an adequate supply of the impurity ions in the flow stream to allow only a small percentage to be extracted in passing through the pre-concentration cell.

The migration of the dissolved ions in the flow stream to the electrodes appears as a leakage current j in the capacitor which is the sum of the partial currents $j_i$ associated with each impurity ion of species i, given by $$j = \sum_i j_i = \sum_i \mu_i n_i \frac{\Phi}{d} = \sigma \frac{\Phi}{d}$$

where $\mu_i$ is the mobility of the impurity ion in the matrix and $n_i$ is its number density, and $\sigma$ is the composite conductivity of the fluid, $\phi$ is the potential applied across the electrodes separated by the distance d. The partial current associated with each ion species is proportional to its number density in the matrix. At very low concentration, it is important to ensure that the impurities are not significantly depleted in order to obtain accurate measurements of the impurity content.

The rate that the impurity ions are extracted per unit time is given by:

$$\Gamma_{ie} = \frac{j_i}{q} A$$

where $q=1.60\times10^{-19}$ Coulomb is the unit charge and A is the ordinary (as opposed to the high specific) surface area covered by the electrode. For purpose of illustration, consider a flow stream that contains only a single species of impurity, therefore, $$\Gamma_{ie} = \frac{j_i}{q} A = \frac{\sigma \Phi}{qd} A = \frac{\mu_i n_i \Phi}{qd} A$$

i.e., the single impurity is the sole contributor to the conductivity of the matrix.

The rate at which the impurity ions are available in the flow stream for extraction is determined by the flow rate F in volume per unit time, and the concentration of the particular impurity. Concentration is defined by $$C = \frac{n_i w_i}{n_f w_f}$$

where $n_i$ and $n_f$ are the number densities of the impurity ion and of the matrix, and $w_i$ and $w_f$ are the atomic or molecular weights of the impurity and the carrier fluid, respectively.

Hence, the rate at which the impurity ions are supplied to the cell is given by:

$$\Gamma_{is} = F n_i = F \frac{w_f}{w_i} C n_f$$

Therefore, the percent of impurity extracted from the flow stream is given by:

$$\varepsilon = \frac{\Gamma_{ie}}{\Gamma_{is}} = \frac{\sigma \Phi}{qd} \frac{w_i}{w_f} \frac{A}{n_f CF} \times 100\%$$

which suggests at first glance that the percent extraction is inversely proportional to the concentration.

However, very importantly, for water with a low concentration of dissolved ions in the ppb range, the conductivity is essentially a linear function of the concentration of the dissolved ions, with typical values in the range of $2\times10^{-9}/$Ohm-cm-ppb, i.e. the conductivity may be approximated as:

$$\sigma \leq 2\times10^{-9} \, C/\text{Ohm-cm}$$

where c is in units of ppb. Substituting for the conductivity $\sigma$ into the expression for $\varepsilon$, we find that the c terms cancel out, and thus that at low concentrations the percent of impurity extracted from the flow stream is independent of the concentration.

Thus, at sub-ppm concentrations:

$$\varepsilon = \frac{\Gamma_{ie}}{\Gamma_{is}} = \frac{\sigma \Phi}{qd} \frac{w_i}{w_f} \frac{A}{n_f CF} \times 100\% \approx 2\times10^{-9} \frac{\Phi w_i A}{qd w_f n_f F} \propto \frac{\Phi A}{dF}$$

It is also worth noting that an optimal size for the interelectrode gap, which was discussed earlier, is specified in terms of the above as:

$$d = \frac{\sigma \Phi}{q\varepsilon} \frac{w_i}{w_f} \frac{A}{n_f CF} \times 100\% \approx 2\times10^{-9} \frac{\Phi w_i A}{q\varepsilon w_f n_f F} \times 100\% \propto \frac{\Phi A}{\varepsilon F}$$

This is an important result for the quantitative determination of the concentration of elements in the flow stream, because it means that the calibration that relates the rate of build up of impurities on the electrodes to the concentration in the flow stream remains constant for all ranges of concentration of interest.

Differently stated, returning now to the detection of more than one species of impurity, this very important approximation means that so long as all the concentrations are in the range where conductivity varies substantially linearly with concentration, with variability governed predominantly by the atomic weight of the impurity species in question, a single flow rate selected to achieve an approximate 1% extraction rate for one species of impurity will also achieve an approximate 1% extraction rate for other species of impurity in this linear variation range, even if the concentrations of the different species are substantially different from one another within that linear variation range.

As a specific example illustrating the foregoing equations, consider Arsenic with atomic weight of 75 amu in a 1 ppb concentration flowing through the preconcentration cell with two electrodes each covering an ordinary surface area of 1 cm$^2$. To avoid any electro-chemical process from occurring, the applied potential needs to be kept below 1 volt. To minimize the amount of water entrained in the cell, the gap spacing should be kept small. From practical considerations, a typical gap spacing might be 1 mm, though the discussion just preceding provides further detail regarding the quantitative optimization of this gap spacing.

The Arsenic ions will then be extracted at the rate on the order of:

$$\Gamma_{ie} = \frac{(2 \times 10^{-9}/\Omega - cm)(1 \text{ Volt})}{(1.6 \times 10^{-19} Coulomb)(0.1 \text{ cm})} \approx 10^{11} \#/\sec$$

To keep the extraction at 1% level, the cell needs to be supplied with $10^{13}$ ions/sec. Hence, the number of water molecules containing the Arsenic impurity at 1 ppb concentration that need to be supplied to the cell to maintain extraction at 1% level is given by:

$$n_f = \frac{w_i}{w_f} \frac{n_i}{C} = \frac{75}{18} \frac{(10^{13} \#/\sec)}{10^{-9}} = 4.17 \times 10^{22} \#/\sec$$

where the molecular weight of the matrix is taken as that of water with a value of 18 amu. The molecular density of water at room temperature is $3.3 \times 10^{22} \#/cm^3$. Hence, the flow rate needed is on the order of:

$$F = \frac{(4.17 \times 10^{22} \#/\sec)}{(3.35 \times 10^{22} \#/cm^3)} = 1.25 \text{ cm}^3/\sec = 1.25 \text{ mL}/\sec = 74.7 \text{ mL}/\min$$

Assuming the flow channel has a cross-sectional area of 0.1 cm$^2$, the flow velocity required would be in the range of 12.5 cm/sec.

In contrast, suppose the arsenic is now in a 10 ppb (i.e., a $10^{-8}$) concentration ten times as much as in the prior example. Arsenic ions will then be extracted at $10^{12}\#/\sec$, requiring a $10^{14}\#/\sec$ supply. With $w_i/w_f$ remaining constant, $n_i/C$ goes from $10^{13}/10^{-9}$ to $10^{14}/10^{-8}$, and $n_f$ remains constant at $4.17 \times 10$ water molecules per second or 75.4 ml per minute. So, in the (typically sub-ppm) range where the conductivity and concentration are linearly related, the flow rate to achieve a 1% extraction remains unchanged, and independent of concentration.

Finally, suppose that in either of the above two examples, one wished to measure lead concentrations in addition to arsenic concentrations. Because the flow rate is independent of concentration in the sub-ppm range, all that changes is that the arsenic atomic weight of 75 is replaced by the lead atomic weight of 207, which is an 207/75-fold increase. The lead ions will also be extracted at $10^{11}$ per second, and so a 1% extraction implies a $10^{13}$ per second supply. However, this means that one would need to flow $(207/75) \times 4.1\ 7 \times 10^{22}$ water molecules per second or 208 ml per minute. If the 4.1 $7 \times 10^{22}$ water molecules per second or 75.4 ml. per minute flow rate is maintained for purposes of a 1% arsenic extraction, then only 1/2.76=0.4% of the lead ions will be extracted, which is certainly an acceptable number. Obviously, for multiple species, one would aim to have a maximum extraction of about 1% (though as noted above one can less preferably go as high as 5%) and would thus pick a flow rate giving an approximately 1% extraction rate to the lightest element to be detected, and thus giving somewhat lower extraction rates to the heavier elements to be detected.

The above values are provided as illustration of the flow rate required to limit the extraction to 1% of the impurity based on the conductivity of the matrix with 1 ppb concentration. At higher concentration levels, the conductivity and hence the extraction rate will be higher. However, there are proportionately more ions in the flow stream such that the percent of ions extracted will be the same at the same flow rate. Hence, the accuracy of the measurement is preserved over the entire range of impurity concentrations (typically sub-ppm) where the conductivity is essentially a linear function of the concentration. Therefore, the dynamic range of this instrument and measurement technique extends over many orders of magnitude of concentration levels from the sub-ppb to the ppm range to provide the same accuracy of measurement, and the variations introduced by differing atomic weights of different impurities species are easily dealt with.

If the extraction procedure is continued indefinitely, the impurities will continue to build up in the double layer. The amount of charge that the capacitor can hold is limited by its capacitance and the capacitor will eventually saturate. Once saturated, no net current will continue to flow. However, ion exchange will continue to take place with the high valence state ions replacing the low valence state ions in the double layer. This ion exchange process will distort the relative concentration of impurity ions trapped in the double layer, thereby distorting the measurement of concentrations in the flow stream.

To preserve the accuracy in interpretation of the data, it is important to avoid saturating the electrode surface. This is one important reason for requiring the electrode to be made of high surface density material such as NCC. Typically, such material is capable of holding 10 mg of foreign material per gm of native material, i.e. approximately 1% by weight, or 10,000 ppm. The detection sensitivity of the XRF technique is on the order of 1 ppm. Therefore, as long as the particular impurity concentration is greater then 0.01% of all the other impurities present, it would be in the detection range of the system. Stated simply, a system as disclosed herein employing NCC electrodes will not saturate until there is 10,000 times as much foreign matter in the NCC as is needed to achieve an XRF detection at a 1 ppm sensitivity.

This saturation can be observed by monitoring the leakage current. When the voltage is first applied to the electrodes, the ions in the immediate vicinity of the electrodes will be collected and appear as a measurable current. When these ions in the immediate vicinity are depleted, then the leakage current will gradually drop to an asymptotic value to reflect the rate at which ions in the flow stream can migrate under the effect of the electric field to the electrodes. This asymptotic leakage current, therefore, is a measure of the total concentration of dissolved ions in the matrix, as long as the electrodes are not saturated. As the electrode approaches saturation, the leakage current will gradually decrease and eventually vanish. Therefore, by monitoring the leakage current, the state of saturation of the electrodes can be monitored.

As stated above, once the electrode surfaces are fully saturated, no net electric current will flow. However, the impurities in the input flow stream 840 will continue to diffuse and can reach the electrodes where the higher valence state ions will replace the low valence state ions. By maintaining the flow after the electrode has saturated, the high valence state impurity ions will eventually build up to a sufficiently high level to become detectable. Since the concentration of the higher concentration impurities can be measured before saturation, the electrochemistry of the sample fluid can be understood, thereby allowing the ion exchange rate between the different impurity ions to be determined. This fact can be exploited using ultra-low trace element measuring means to detect and measure the concentration of ultra-low trace, high valence ions in high conductivity fluids such as electrolytes, based on detecting the saturation state via the leakage current.

As discussed above, because extraction rates are kept low, the concentrations of impurities in the feed stream are not altered by more than a few percent at most. The ions are only captured until the analysis period is completed and then they are returned to the media from whence they came, as discussed further in connection with FIG. 18. The invention disclosed herein requires only a small amount of NCC material in a single cell, because it is only used for detection and not removal. It can be configured to be controlled remotely over a telecommunications link, either directly, or by wireless means or via networks such as the Internet. The preferred system-specific operational user interface software is currently constructed in the LabView™ architecture, a commercial program that allows for integrated control of hardware and software. LabView provides the means to set operating parameters and run the system via a virtual interface on a computer system connected to the system directly or remotely such as through the Internet or by wireless means. Alternatively, other terminal emulator programs can be employed, such as PC-anywhere and Timbuktu, or custom developed software to remotely control the system operation. Regardless of the means, because the operation of the present invention is capable of being fully automated, it can be controlled from remote locations. The remote operator would have all of the capabilities of an on-site operator such as system startup, emergency stop, test specifications, data analysis, data download and data review. The system can also be configured to operate automatically, reporting results of the analysis to remote locations. To prevent from unauthorized tempering, access to the operation of the system can be protected by password control. Obviously, the system would benefit from advances in remote computer communication technology and therefore the technology described above is a means of example and the present invention is not limited to the use thereof.

Figure 17:
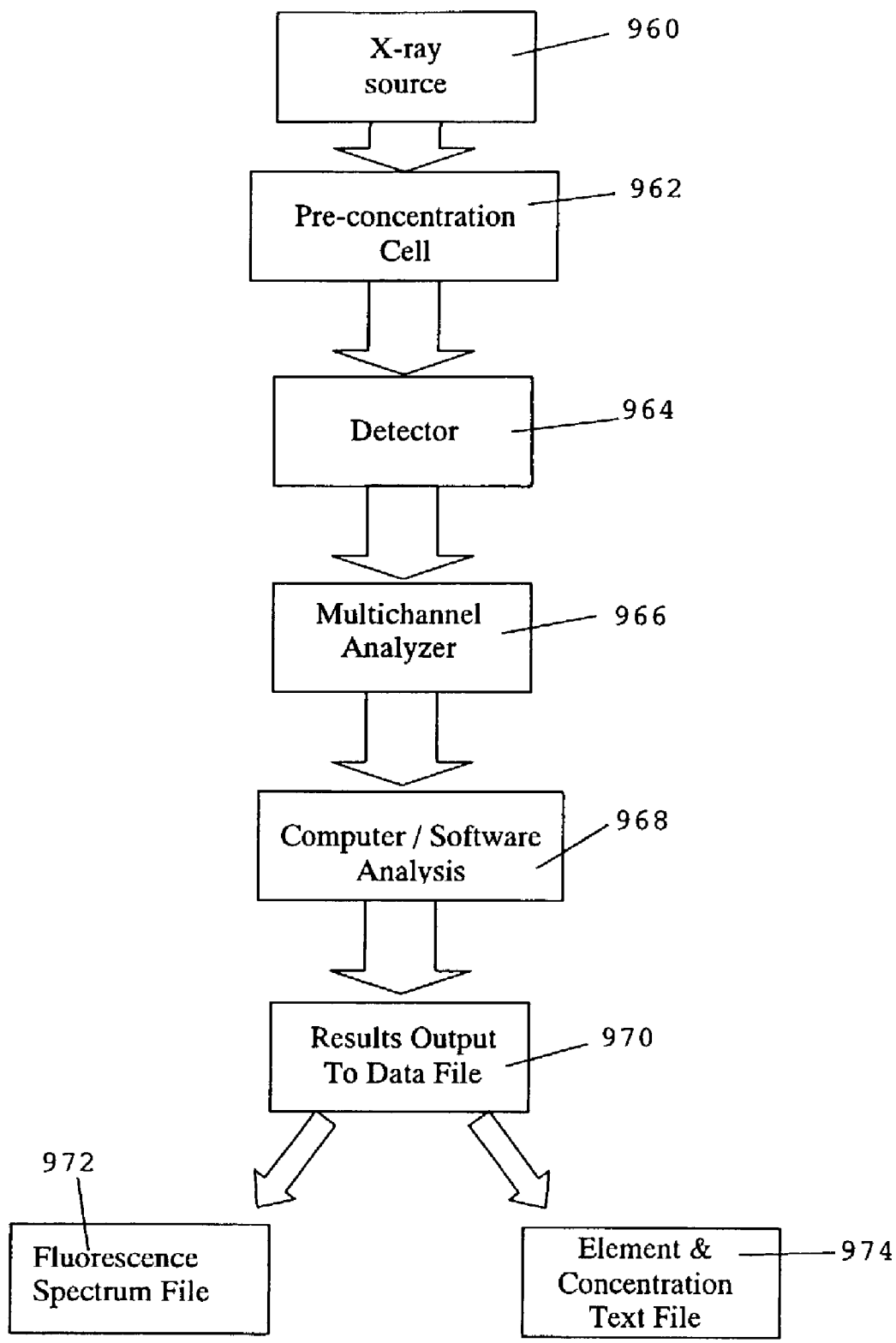
FIG. 17 is a flow chart detailing the measurement and analysis system operation when conducted during preconcentration.

During or after the pre-concentration cycle described in FIG. 15, x-ray fluorescence is used to analyze the ions collected in the cell 112. FIG. 17 is a flowchart describing the measurement and analysis process in this system when this x-ray analysis is preformed during the preconcentration cycle. At block 960 the x-ray source emits the x-ray energy and it is directed towards the pre-concentration cell 100. At block 962, the sample fluid flows through the pre-concentration cell 100, and the electric potential draws dissolved metallic ions to their preferential high surface area electrode 218 or 220, either positive or negative. The energy from x-ray source means 644 is sufficient to fluoresce the captured ions, which then radiate at a lower energy than the excited source energy, characteristic of the ionic species. At block 964, this fluoresced signal is captured by the detector means 648. At block 966, the detector signal is processed by the multichannel analyzer 652, and subsequently sent to the host computer 654 for automated software analysis in block 968. This system utilizes a standard computational system with system specific operational software and automated data analysis software. The computer can pass through the data from the multichannel analyzer directly to block 970 where the intensity spectrum can be stored, or process the data in real-time with the analysis software. The automated analysis software assesses the fluorescence data provided by the multichannel analyzer 652 and identifies the intensity peaks associated with the elements in accordance with their characteristic fluoresce photon energy to output their concentration in the sample fluid based on the duration of concentration and the calibration values associated with the particular concentration cell. The x-ray analysis results are stored in block 970 for later retrieval. The end user can select to retrieve the data, for example, as a fluorescence spectrum file as in block 972 or, for example, as analyzed data showing element and concentration as in block 974. Concentration can be shown, for example, as a percent of the total or as a "part per" number.

As a monitoring instrument, the user can also preset certain predetermined threshold concentration values for the system to sound an alarm or trigger certain corrective or preventive actions automatically when the threshold value is exceeded (triggering means for triggering an action when the system detects that a concentration of at least one element of interest in said fluid has passed i.e., dropped below or exceeded a predetermined threshold concentration). For example, not limitation, an alarm can be employed for process fluids where a dissolved element is depleted by the process or builds up in the stream and needs to be automatically monitored and adjusted if the concentration falls outside of a specified range of values, and the action of either injection of concentrated material into the stream or dilution of the stream based on the alarm is utilized to maintain the specified values. That is, the triggering means may trigger injecting at least one element (the detected element or another element) into the fluid, and/or it may trigger diluting at least one diluting fluid (more of the original fluid, or a different fluid) into the fluid.

Figure 18:
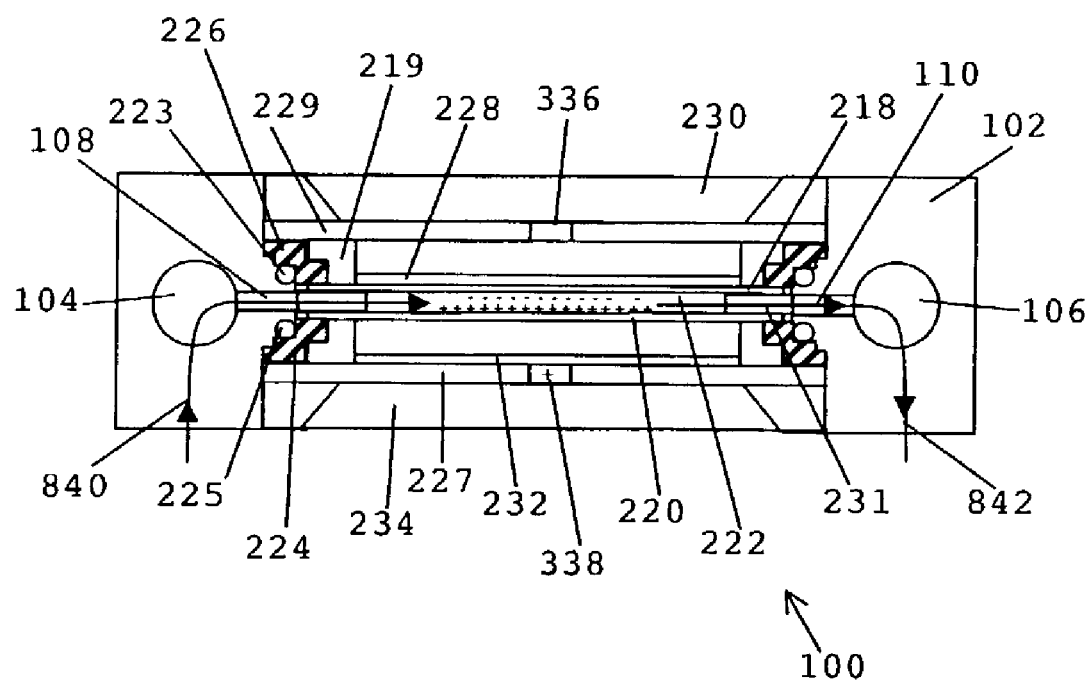
FIG. 18 is a front cross-sectional view illustrating the cleaning of the pre-concentration cell.

As shown in FIG. 18, at the end of the measurement cycle, the high surface area electrodes 278 and 220 are electrically shorted. As a result of employing such ionic release means for cleaning said preconcentration cell after use, the double layer disappears and the captured ions are released back into the output fluid flow 842 through the central flow interelectrode gap 222, such that they are returned to the media from whence they came. This resets the pre-concentration cell 100 to its initial state and thus completes the full cycle. The call can thereafter be reused.

While the invention disclosed herein is intended to provide impurity measurements on site and can be installed on-line for continuous monitoring of the impurity concentrations in a flow stream, the pre-concentration cell can also function in a stand-alone mode to take samples at remote sites. This is independent of the X-ray and other testing, monitoring, detection, communications, and analysis equipment that further facilitates use of the pre-concentration cell. These remotely-gathered samples are then characterized by the X-ray source and detector/multi-channel analyzer system and procedures disclosed herein after the sampling is complete. Simply stated, samples can be collected in the cells themselves without all of the other equipment needed for testing and analysis, and the cells can then be moved to a different location for follow up testing and analysis.

As discussed in detail earlier, prior to its use for testing, each pre-concentration cell is first characterized (calibrated) to establish the background, sensitivity, and ion extraction rate. The pre-concentration cell, along with the voltage application, flow control, and leakage current monitoring hardware can be designed to be removable from the system to operate in a stand-alone mode. The pre-concentration cell can then be connected to any flow stream through standard flow connectors to sample the flow stream for a predetermined period of time based on estimated concentration of impurities in the flow stream determined from the leakage current observed. Upon completion of the sampling period, the outlet and intake valves on the pre-concentration cell are shut off, in that order, to trap some of the flow stream in the cell before disconnecting from the source. The electrodes preferably remain charged by transportable voltage supply 385 to be shortly discussed, or the voltage may be turned off. In the absence of an applied voltage, the ions trapped in the double layer will, however, return to the fluid trapped in the cell, and a voltage will then need to be reapplied later on to re-form the double layer on the electrodes. The pre-concentration cell can then be inserted into the complete system x-ray system to measure the impurity concentrations in the cell.

A transportable preconcentration cell 101 suitable for this alternative operating method of sampling in an environment where x-ray source and/or detector equipment is not immediately available is shown in FIG. 19. In this method, the pre-concentration cell is configured for stand alone operation in order to collect the ionic particles at any desired location. After the preconcentration is complete, the pre-concentration cell is capped with the fluid inside and a voltage continuing to be applied, and transported to a laboratory or alternative environment equipped with the x-ray source, detector and analyzing system described above in FIG. 14.

Thus, as shown in FIG. 19, similarly to the preconcentration cell 100 of FIG. 13, transportable preconcentration cell 101 includes cell body 102, inlet flow port 104, inlet flow valve 380, outlet flow port 106, inlet flow slot 108, electrode assembly 112, fasteners 109, outlet flow slot 110, outlet flow valve 382, valve control 384, electric potential and current meter 386, and leakage current monitoring means 388. However, this transportable preconcentration cell 101 also comprises a transportable voltage supply 385 such as but not limited to one or more batteries or fuel cells, a control chip 387, a positive voltage cell lead 381, and a negative voltage cell lead 383. The transportable voltage supply 385 and control chip 387 are preferably embedded into cell body 102 and connected to leads 381 and 383 in order to minimize the need for excess space and to work integrally with the x-ray source and XRF detector in the same configuration as the pre-concentration cell 100 earlier shown in FIG. 13. In a less preferred embodiment still within the scope of the invention, transportable voltage supply 385 and control chip 387 are maintained as separate modules attachable to the cell of FIG. 13 so as to supply the voltage.

Figure 20:
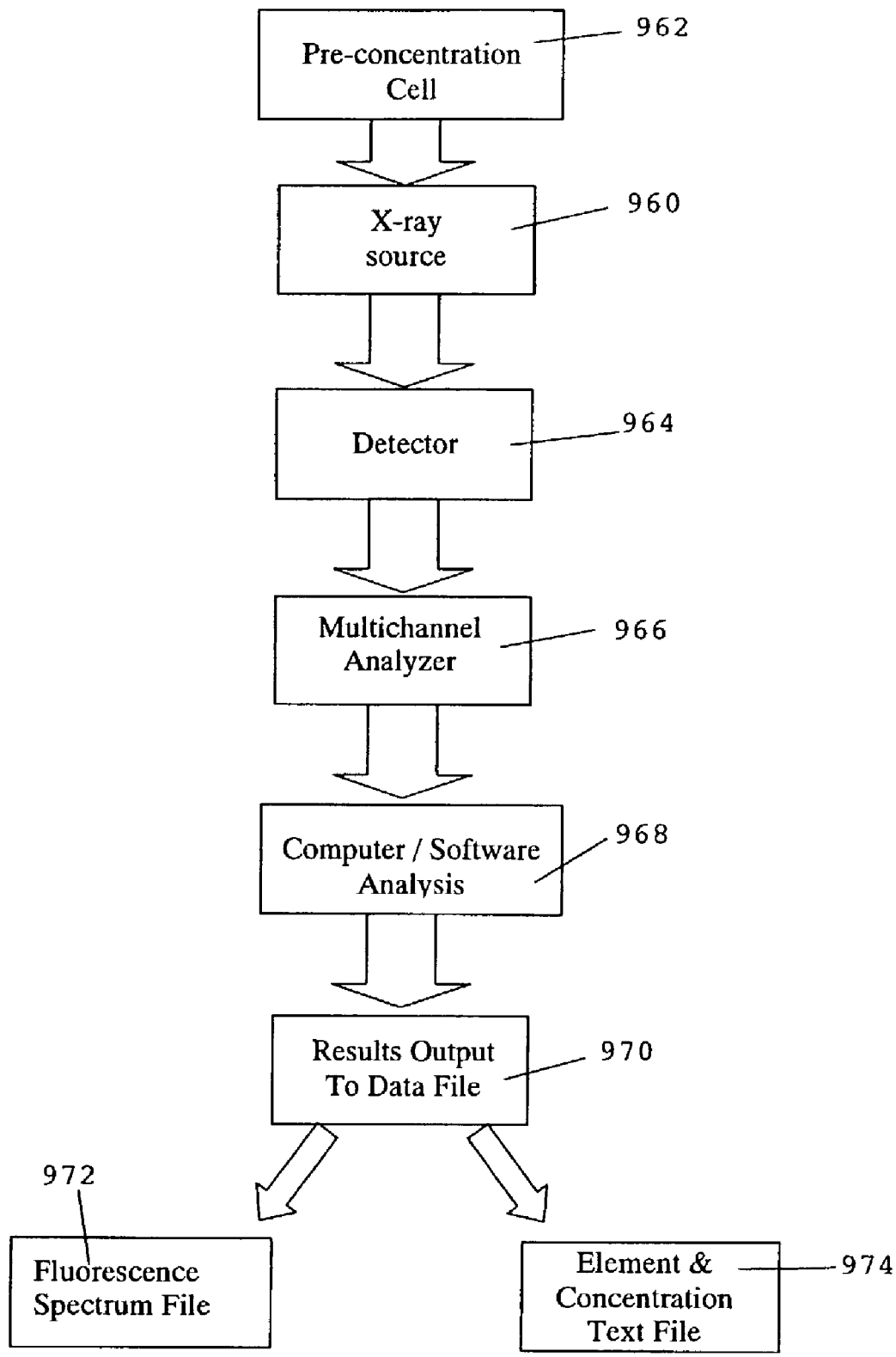
FIG. 20, in contrast to FIG. 17, is a flow chart detailing the measurement and analysis system operation when conducted after preconcentration.

The operation of transportable cell 101 follows the flow chart in FIG. 20. First, fluid flows through the cell and ions are captured in the preconcentration cell with voltage applied and maintained through voltage application means 389, which may comprise voltage from an external voltage source, or voltage from transportable voltage supply 385.

Once preconcentration is complete, the cell is capped to keep the fluid and ions inside, and the voltage is either smoothly cut over from the external voltage source to the transportable voltage supply 385, or, if transportable voltage supply 385 was used all along, application of the voltage from transportable voltage supply 385 is simply maintained. This is all designated generally at block 962. This capping and continued application of a voltage maintains the ions in the double layer formation after preconcentration and throughout transport, and allows the cell to be transported to a laboratory with the necessary x-ray equipment shown in FIG. 14 to conduct immediate measurement and analysis without having to apply a voltage to re-entrain the ions in the electrodes via double layer formation.

It should be observed, while the cell of FIG. 19 is transportable due to the transportable voltage supply 385 which allows application a voltage across the electrodes during transport, that this cell can most certainly be used with the method described in FIG. 17 with the x-rays applied during preconcentration, wherein the voltage application means during preconcentration comprises transportable voltage supply 385 rather than some external voltage source. In other words, if desired, transportable voltage supply 385 can supply the voltage for preconcentration even when no transport is required, and can also be used for entrainment maintenance when transport is required.

Once preconcentration cell 101 has been transported to a laboratory with necessary x-ray equipment, it is exposed to x-rays via x-ray source 644, as designated by block 960. The x-ray fluorescence emissions from the pre-concentration cell are then collected by detector 648, as designated by block 964. Thereafter, processing proceeds through blocks 964, 966, 968, 970, 972, and 974 in substantially the same manner as was earlier illustrated and described in connection with FIG. 17. When everything is complete, cleaning of the cell proceeds in the same manner as in FIG. 18.

At this point, we will discuss some further quantitative considerations pertaining to this device, system and method, in order to provide a better idea of how all of the operational parameters relate to one another, to the samples being tested, and to the measurements that are desired.

As discussed above, the thickness of the electrode nearer to the source and detector should not exceed the optical depth of the photon to be detected, that is, this thickness should be less than or equal to.

The interelectrode gap, in turn, is determined by the pressure/flow rate conditions and the partial conductivity of the ions of interest. The Kapton windows can support about $\frac{1}{10}$ atm. without excessive bowing (<100 microns). To limit the impurity extracted from the flow stream to around 1% of its initial value, with the applied voltage limited to approximately 1 Volt and a typical gap spacing of 1 mm, the flow rate needs to be at 1.5 mL/sec. or 90 mL/min. through a cell with a typical volume of 0.1 cm$^3$. This is well within the flow rates achievable with $\frac{1}{10}$ atm. inlet pressure for a cell volume defined by a 1 cm$^2$ window substantially matching the XRF interrogation spot area and a cell interelectrode gap of 0.1 cm.

Based on the known strength of Kapton and the thickness chosen, the window can support the pressure for flow rates significantly greater than the 90 mL/min required to maintain extraction well below 1%. Increasing the flow rate, however, does not increase the concentration time required to reach MDL. The concentration time required to reach MDL is given by:

$$t = \frac{N_t}{\Gamma_{ie}}$$

where $N_i$ is the number of impurity ions captured by the electrodes required for detection, and $\Gamma_{ie}$ is the rate these are extracted from the flow stream.

The number of impurity ions needed for detection is determined by the sensitivity of the instrument. Detection sensitivity, like impurity concentration, is usually defined in terms of mass ratio as:

$$S = \frac{N_i w_i}{V_c n_c w_c}$$

where $V_c$ is the volume of the host material in the cell with number density $n_c$ of atomic weight $w_c$. Since most of the signal and background arise from the "upper" electrode closest to the "upper" window, $V_c$ can be estimated as the volume of the first NCC electrode with ordinary surface area A and thickness. If the electrode is filled with water, its number density and molecular density can be taken as that of water, $n_c = n_f = 3.3 \times 10^{22}$ #/cm$^3$ and $w_c = w_f = 18$.

The extraction rate is previously given as:

$$\Gamma_{ie} = \frac{\sigma \Phi}{qd} A$$

Making the substitution into the time required to reach MDL, the resulting expression is:

$$t = \frac{w_f}{w_i} \frac{S l n_f q d}{\sigma \Phi} \propto \frac{Sl}{\sigma} \propto \frac{Sl}{C}$$

i.e., the concentration time required to reach MDL is directly proportional to the detection sensitivity of the instrument S and the thickness of the electrode, and inversely proportional to the conductivity of the matrix σ. To understand the final proportionality, recall the important result that for low impurity concentration in the sub-ppm range, the conductivity is a linear function of the concentration that can be represented approximately as $\sigma \approx 2 \times 10^{-9}$ c/Ω-cm, where c is in units of ppb. Therefore, the concentration time required to reach MDL is inversely proportional to the concentration as is to be expected. Similarly, if the sensitivity of the system is poor, i.e. S is numerically larger, or if the electrode thickness is excessive to introduce more host material, the concentration time needed becomes longer. Note also that increasing the flow rate does not reduce the required concentration time, as has already been concluded, but does improve the accuracy of the measurement by reducing the change in concentration of the matrix, that is, by extracting a smaller percentage ε of contaminants. It is also worth noting that the time required to reach MDL is also independent of the ordinary surface area A covered by the electrode. This is because increasing the area increases the collection rate as well as the amount of host materials proportionately.

As an example, consider again the concentration of 1 ppb arsenic in water in a cell with electrodes measuring 1 cm$^2$ by 100 micron thick separated by a distance of 2 mm with 1 Volt applied across them. The conductivity of the matrix with 1 ppb concentration is $2 \times 10^{-9}$/Ω-cm. Substituting these values into the expression for concentration time needed to reach MDL for an instrument with sensitivity $S = 10^{-6}$ (i.e. 1 ppm):

$$t = \frac{(18 \text{ amu})}{(75 \text{ amu})} \frac{((10^{-6})(2 \times 10^{-2} \text{ cm})(3.33 \times 10^{22} \text{ cm}^{-3})}{(1.6 \times 10^{-19} \text{Coulomb})(10^{-1} \text{ cm}))}{((2 \times 10^{-9}/\Omega - \text{cm})(1 \text{ Volt}))} = 1.28 \times 10^4 \text{ sec}$$

Therefore, to detect Arsenic in a matrix with a 1 ppb concentration may require 4 hours of concentration time. However, for 10 ppb, which is the current international standard for acceptance of As concentration in drinking water, the concentration time required is only one-tenth as long, i.e., approximately 25 min.

One question that arises particularly when one does not know a priori what concentration to expect is how long to run the cell? In many situations, the user will have a target MDL, for example, the user may wish to see if arsenic in a drinking water supply exceeds the EPA limit of 10 ppb. Thus, the user runs the cell for the length of time necessary to detect 10 ppb e.g., 25 minutes under the scenario described in the preceding paragraph and if there is nothing detected, then the user knows that the arsenic is below the EPA level. Thus, the concentration time here is based on the time required to accumulate a concentration up to a target MDL, that is, it is based on setting the impurity concentration c to a predetermined desired concentration detection level and then deducing the required concentration time accordingly. This timing control means can be automated, or can be manual.

Whether timing control is automated or manual, this means, in sum, that one can control how long the fluid flows through said ionic preconcentration cell based on setting an impurity concentration c, in a range where conductivity varies substantially linearly with concentration, to a predetermined desired concentration detection level and flowing the fluid for a time t given by:

$$t \propto \frac{Sl}{\sigma} \propto \frac{Sl}{C}$$

wherein S designates a sensitivity of the x-ray detection system; designates a thickness of the upper high surface area electrode; and σ designates a composite conductivity of the fluid.

In a different situation (with no target MDL), one could simply let the system run to saturation and then stop and obtain whatever sensitivity readings are yielded at saturation. In particular, there is a linear relationship between time and sensitivity which holds as long as saturation is not reached. The user would generally know which sensitivity is desired and would proceed on that basis. However, a monitoring of the leakage current alerts the user as to when saturation is approaching and the numbers might then not be as accurate as desired. Since the data is taken as a time series, this detection of the leakage current can then be used to "stop" the fluid flow (by the user or by the control system)

to obtain the best/most reliable result, or more generally to control the period of time for which the fluid flows.

The function of the pre-concentration cell is to concentrate the impurities to facilitate their detection and quantitative measurement by identifying intensity peaks associated with the characteristic energy of the fluorescence photons in the spectrum. By maintaining a constant flow rate and keeping the extraction ratio small, the rate of concentration is constant and roughly independent of flow rate, as discussed above. Therefore, by reference to the established calibration and scaling values, the concentration in the sample can be related quantitatively to the concentration in the flow stream through lookup tables stored in the computer. For detection of different elements, the energy of the primary x-ray may be varied to maximize signal to noise ratio.

An example of the static operation of an XRF follows: In a region of the spectra where one would measure arsenic, the photon scattering into the continuum from the described window/water/NCC system (as an example, using a cell designed for atomic number 30, 4 cm$^2$ by about 0.2 cm thick) contributes about 0.5 counts/min/eV and the signal in the peak of the 1 ppm (0.8 $\mu$ grams) arsenic K-line is also about 0.5 counts/min/eV. After about 20 min the peak height is about ten counts as is the continuum. The fluctuation in the continuum is about three counts which yields a signal to noise of about 10/3 or three.

An example of the dynamic operation of an XRF follows: A 10 ppb solution of As in water would contain 0.01 microgram of As per cc of water and at a 120 cc/min (2 cc/sec) flow rate would be available at a rate of 1.2 micrograms/minute. The conductivity of such a solution is about 2*10$^{-8}$ mho/cm. The resulting current is made up of both anions and cations so half of the current provides the ion deposition rate. With cell dimensions of 4 cm$^2$*0.15 cm (area*gap) and applying 1.5 volts, one would deposit 2.4*10$^{12}$ ions/sec or 0.3 nanograms/sec or 18 nanograms/min. To deposit 0.8 micrograms would require 45 minutes and removes approximately 1.5% of the original As. The continuum background would grow linearly with time but both the signal and the amount of As deposited would grow linearly with time, hence the signal would grow quadratically with time. That is, 0.018 micrograms/sec*t*(0.5 cnts/min/eV/0.8 micrograms)*t=13.7 counts/eV for the signal at 35 minutes and the noise is sqrt (0.5 counts/min/eV*t)=4.2; thus 13.7/4.2=Signal/Noise=3.3 at 35 minutes. This crude analysis uses peak to background for the signal to noise. A more sophisticated peak fitting/peak area analysis would show similar but better quantitative results.

Finally, once a cell has been used, it is necessary to clean the cell for its next use by purging the captured ions back into the fluid stream from whence they came. Various ionic release means for cleaning said preconcentration cell after use can be used to cleanse the cell automatically. They include removal of the applied voltage, temporary reversal of the applied voltage, or simply by shorting out the two electrodes. These techniques can be used in sequence or by themselves, depending on the structure of the electrode material and the level of impurity concentrations on their surfaces. The cleansing process returns all of the captured ions to the fluid stream. As the amount returned is no greater than the amount removed and this stream is usually of a smaller volume than the original stream, the transient increased concentration is negligible.

In an alternative embodiment of preconcentration cell 100 shown in FIG. 21, the inlet flow means comprises inlet flow slot 990 and the outlet flow means comprises outlet flow slot 992 respectively, but in a configuration differing somewhat from that of FIG. 1. In a further alternative embodiment shown in FIG. 22, the inlet flow means comprises an array of a plurality of inlet flow tubes 990 and the outlet flow means comprises an array of a plurality of outlet flow tubes 992. The array of inlet flow tubes 990 and the array of outlet flow tubes 992 both comprise a series of passageways of substantially circular cross section bored in the same plane as the central flow interelectrode gap 222 which are all substantially parallel to each other with substantially equal spacing therebetween. The cross-sectional shape of inlet flow tubes 990 and outlet flow tubes 992 and their spacing and parallelism can be varied at will within the scope of this disclosure and its associated claims so long as these tubes permit the aqueous solution being tested to properly flow therethrough.

Aligned with the each of the inlet flow tubes 990 and the outlet flow tubes 992 of FIG. 22, but on diametrically opposite sides of inlet port 104 and outlet port 106, are a series of optional inlet flow channel access holes 994 and outlet flow channel access holes 996 respectively. These flow channel access holes 994 and 996 are an example of how to provide a debris cleaning means for cleaning debris from the inlet and outlet flow means, as necessary. Flow channel access holes 994 and 996 are closed and unused during the operation of the pre-concentration cell 100.

Figure 23:
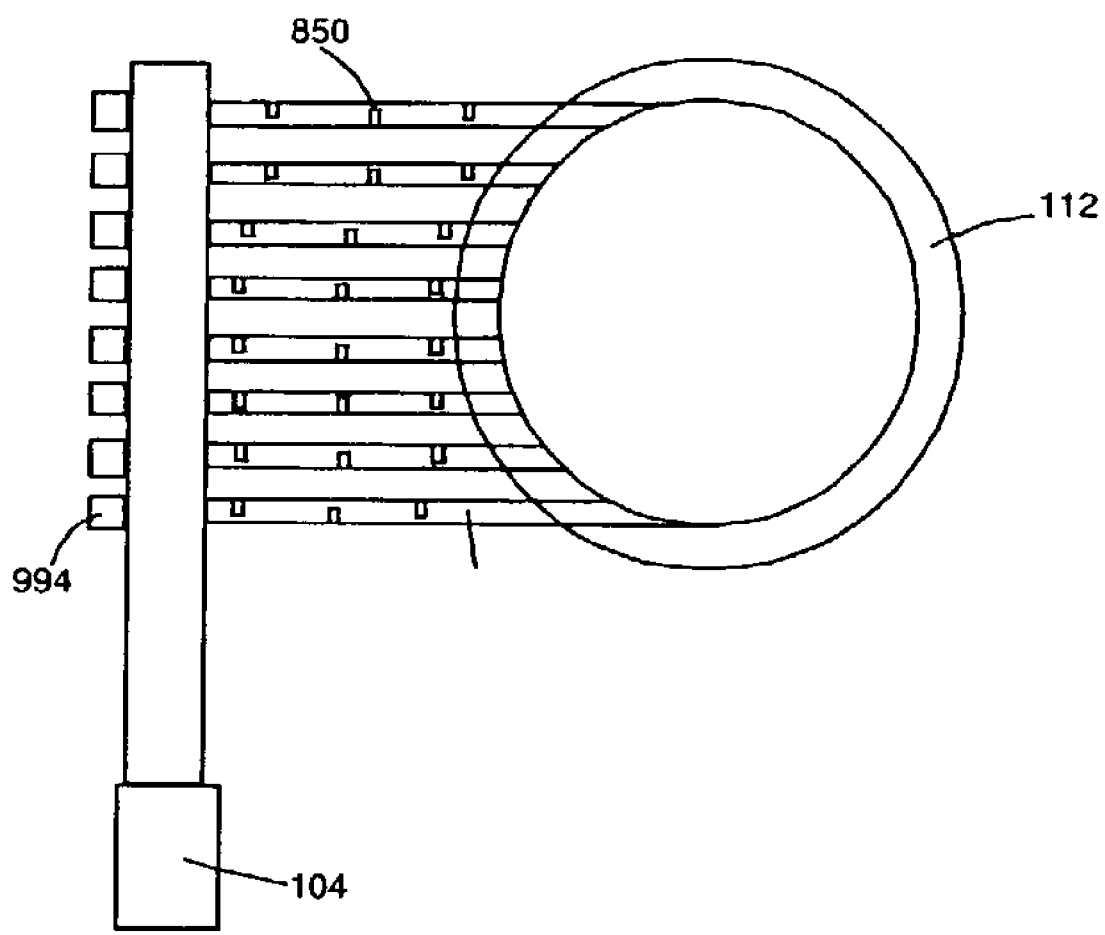
FIG. 23 is a top view of an alternative embodiment of the pre-concentration cell with flow turbulence enhancers.

Additionally, inlet flow tubes 990 of the pre-concentration cell 100 optionally comprise flow turbulence enhancement means 850 for enhancing the turbulence of the input fluid flow 840, thereby inducing mixing of the flow stream to allow the impurities to be more uniformly extracted from the flow stream passing through the concentration cell. Such flow turbulence enhancement means can also accompany the embodiments utilizing flow slots as opposed to flow tubes. As shown in FIG. 23, the flow turbulence enhancement means 850 are arranged all along the array of input flow tubes 990 of the pre-concentration cell 100. Although the flow turbulence enhancement means 850 shown in FIG. 21 are illustrated as tabs placed on a diagonal at even intervals, they can actually be any shape and placed in any distribution that would be known to someone of ordinary skill for enhancing flow turbulence.

While only certain preferred features of the invention have been illustrated and described, many modifications, changes and substitutions will occur to those skilled in the art. It is, therefore, to be understood that this disclosure and its associated claims are intended to cover all such modifications and changes as fall within the true spirit of the invention.

The invention claimed is:

1. A system for identifying and measuring concentrations of elements in fluids, comprising:
   an ionic preconcentration cell, comprising:
      an upper high surface area electrode having a high specific surface area thereof;
      a lower high surface area electrode having a high specific surface area thereof, substantially parallel to said upper high surface area electrode;
      a central flow interelectrode gap separating said upper and lower high surface area electrodes by a predetermined interelectrode gap width; and
      fluid flow means for flowing a fluid through said central flow interelectrode gap;
   a computerized apparatus comprising calibration data related to a rate at which photons emitted from said preconcentration cell based are detected on a fluid of interest containing a known concentration of at least one element of interest being flowed at a known flow rate through said central flow interelectrode gap for a known period of time, a known voltage differential being applied across said electrodes, and said preconcentration cell being exposed to x-rays; and said computerized apparatus deducing an identity, or measurement of concentration, of an unknown concentration of said at least one element of interest in said fluid of interest, based on comparing said calibration data with test data related to a rate at which photons emitted from said preconcentration cell are detected based on said fluid of interest with said unknown concentration being flowed at a known flow rate through said central flow interelectrode gap for a known period of time, a known voltage differential being applied across said electrodes, and said preconcentration cell being exposed to x-rays.

2. The system of claim 1, further comprising:
voltage application means for applying a voltage differential between said upper high surface area electrode and said lower high surface area electrode while said fluid is flowing through said central flow interelectrode gap.

3. The system of claim 2, said voltage application means further comprising:
a transportable voltage supply connected across said upper and lower high surface area electrodes for applying an electrostatic charge across said electrodes and thereby maintaining ions from said at least one element entrained in said electrodes during transport of said ionic preconcentration cell.

4. The system of claim 3, wherein:
said transportable voltage supply is embedded into a body of said ionic preconcentration cell.

5. The system of claim 2, said central flow interelectrode gap having said predetermined interelectrode gap width, designated d, within an interelectrode gap range specified by:

$$d = \frac{\sigma\Phi}{q\varepsilon}\frac{w_i}{w_f}\frac{A}{n_f CF} \times 100\% \approx 2 \times 10^{-9}\frac{\Phi w_i A}{q\varepsilon w_f n_f F} \times 100\% \propto \frac{\Phi A}{\varepsilon F},$$

wherein:
$\varepsilon$ designates a predetermined percentage of at least one element of interest to be extracted from said fluid, $\sigma$ designates a composite conductivity of said fluid, $\Phi$ designates a potential applied by said voltage application means across said electrodes, $q=1.60\times10^{-19}$ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, c designates a concentration of said at least one element of interest in said fluid, and F designates a flow rate of said fluid through said ionic preconcentration cell;

said high surface area electrodes further having said ordinary surface area A approximately equal to an interrogation spot area of x-rays to which said preconcentration cell is to be exposed;

said $\varepsilon$ is chosen to be below approximately 5% for said at least one element of interest;

said $\Phi$ is chosen to be below an electrochemical potential of said at least one element of interest and below an electrolysis potential of said fluid;

said F is chosen to exert no more than approximately 0.1 atm of pressure upon an upper x-ray transmission window of said ionic preconcentration cell in intimate contact with an upper surface of said upper high surface area electrode;

said $n_f$ and said $w_f$ are chosen with reference to said at least one element of interest; and said $w_i$ is chosen with reference to said fluid.

6. The system of claim 5, said central flow interelectrode gap having said predetermined interelectrode gap width, d, with:
a minimum gap width selected from a minimum gap width group consisting of 2 mm, 1 mm, 0.5 mm, and 0.25 mm; and
a maximum gap width selected from a maximum gap width group consisting of 2 mm, 5 mm, and 10 mm.

7. The system of claim 2, said calibration data further comprising:
ion extraction rate data related to a rate at which photons emitted from said preconcentration cell are detected, when a calibration solution, containing said at least one element of interest in a fluid of interest in known concentration below a minimum detection level of x-ray detection equipment to be used for said detecting and measuring, is flowed through the central flow interelectrode gap of said preconcentration cell, at a substantially constant flow rate, while the voltage application means applies the voltage differential across the electrodes of said preconcentration cell, below an electrochemical potential of said at least one element of interest and below an electrolysis potential of said calibration solution, and when said preconcentration cell is exposed to x-rays.

8. The system of claim 2, said calibration data further comprising:
background data related to a rate at which photons emitted from said preconcentration cell are detected, when said preconcentration cell is filled with a highly purified form of a fluid of interest and exposed to x-rays;

sensitivity data related to a rate at which photons emitted from said preconcentration cell are detected, when said preconcentration cell is filled with a first calibration solution, containing at least one element of interest in said fluid of interest in known concentration above a minimum detection level of x-ray detection equipment to be used for said detecting and measuring, and when said preconcentration cell is exposed to x-rays; and ion extraction rate data related to a rate at which photons emitted from said preconcentration cell are detected, when a second calibration solution, containing said at least one element of interest in said fluid of interest in known concentration below said minimum detection level of x-ray detection equipment to be used for said detecting and measuring, is flowed through the central flow interelectrode gap of said preconcentration cell, at a substantially constant flow rate, while the voltage application means applies the voltage differential across the electrodes of said preconcentration cell, below an electrochemical potential of said at least one element of interest and below an electrolysis potential of said second calibration solution, and when said preconcentration cell is exposed to x-rays.

9. The system of claim 8, further comprising:
test data accumulation means for obtaining said test data comprising data related to a rate at which photons emitted from said preconcentration cell are detected when said fluid, suspected to contain at least one element of interest, is flowed through said central flow interelectrode gap at a substantially constant flow rate, while said voltage application means applies said voltage differential across said electrodes below an electrochemical potential of said at least one element of interest and below an electrolysis potential of said fluid, and when said preconcentration cell is exposed to x-rays.

10. The system of claim 9, further comprising:
analysis means for analyzing said test data in relation to said background data, said sensitivity data, and said ion extraction rate data, and deducing therefrom a concentration in said fluid, if any, of the suspected at least one element of interest.

11. The system of claim 2, further comprising:
test data accumulation means for obtaining said test data comprising data related to a rate at which photons emitted from said preconcentration cell are detected when said fluid, suspected to contain at least one element of interest, is flowed through said central flow interelectrode gap at a substantially constant flow rate, while said voltage application means applies said voltage differential across said electrodes below an electrochemical potential of said at least one element of interest and below an electrolysis potential of said fluid, and when said preconcentration cell is exposed to x-rays.

12. The system of claim 11, further comprising:
analysis means for analyzing said test data and deducing therefrom a concentration in said fluid, if any, of the suspected at least one element of interest.

13. The system of claim 2, said voltage application means further comprising:
a transportable voltage supply for applying an electrostatic charge across said electrodes and thereby maintaining ions from said at least one element entrained in said electrodes during transport of said ionic preconcentration cell: after ceasing flow of said fluid, while transporting said ionic preconcentration cell to an x-ray source means for emitting x-rays toward said preconcentration cell, and while exposing said preconcentration cell to x-rays.

14. The system of claim 2, further comprising flow control means for:
controlling a flow rate F of said fluid through said ionic preconcentration cell and maintaining said F at a substantially constant level so as to maintain $\epsilon$, which designates a predetermined percentage of at least one element of interest to be extracted from said fluid and is specified by:

$$\varepsilon = \frac{\Gamma_{ie}}{\Gamma_{is}} = \frac{\sigma \Phi}{qd} \frac{w_i}{w_f} \frac{A}{n_f CF} \times 100\%,$$

below approximately 5% for said at least one element of interest; wherein:
$\Gamma_{ie}$ and $\Gamma_{is}$ designate rates at which ions of said at least one element of interest are respectively extracted from said fluid by said cell and supplied to said cell by said fluid, $\sigma$ designates a composite conductivity of said fluid, $\Phi$ designates a potential applied by said voltage application means across said electrodes, d designates said predetermined interelectrode gap width of said central flow interelectrode gap, $q=1.60\times10^{-19}$ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, and c designates a concentration of said at least one element of interest in said fluid; and
for having said concentration c in a range where conductivity varies substantially linearly with concentration, with c in units of parts per billion, wherein $\sigma$ is approximated by:

$\sigma \approx 2\times10^{-9}$ C/Ohm-cm.

15. The system of claim 14, wherein said $\epsilon$ is maintained below an extraction percentage selected from an extraction percentage group consisting of approximately 4%, 3%, 2%, and 1%.

16. The system of claim 2, said voltage application means applying said voltage differential across said electrodes below an electrochemical potential of at least one element of interest and below an electrolysis potential of said fluid.

17. The system of claim 1, said ionic preconcentration cell further comprising:
an upper x-ray transmission window in intimate contact with an upper surface of said upper high surface area electrode.

18. The system of claim 17, said ionic preconcentration cell further comprising:
a lower x-ray transmission window in intimate contact with a lower surface of said lower high surface area electrode.

19. The system of claim 18, said lower x-ray transmission window having:
an atomic number below 10;
structural rigidity to support up to $\frac{1}{10}$ atm. of pressure without bowing more than approximately 100 microns;
substantial impermeability relative to said fluid;
x-ray transparency greater than 90% for characteristic photon energies from an element of interest for which a fluidic concentration is to be measured;
x-ray scattering therefrom minimized to less than approximately 10% of radiation scattered from a column of said fluid equal to one optical depth in said fluid of a characteristic photonic energy from an element of interest for which a fluidic concentration is to be measured; and
freedom from any single contaminant in excess of 1 part per million, when measured by x-ray fluorescence.

20. The system of claim 18, said lower x-ray transmission window comprising a polyimid film having structural rigidity to support up to $\frac{1}{10}$ atm. of pressure without bowing more than approximately 100 microns.

21. The system of claim 17, said ionic preconcentration cell further comprising:
a cell collector body maintaining a position of said upper and lower high surface area electrodes and said upper x-ray transmission window relative to one another, said cell collector body in turn comprising a material having:
substantially no conductivity;
resistance to ionic leaching; and
resistance to radiation degradation from x-rays to which said preconcentration cell is to be exposed.

22. The system of claim 17, said ionic preconcentration cell further comprising:
a cell collector body maintaining a position of said upper and lower high surface area electrodes and said upper x-ray transmission window relative to one another, said cell collector body comprising a material selected from a material group consisting of: plastic, glass, and fiberglass.

23. The system of claim 17, said ionic preconcentration cell further comprising:
a cell collector body maintaining a position of said upper and lower high surface area electrodes and said upper x-ray transmission window relative to one another, said cell collector body comprising a non-conducting, machinable polymer substantially resistant to radiation degradation.

24. The system of claim 17, said upper x-ray transmission window having a surface area approximately equal to an interrogation spot area of x-rays to which said preconcentration cell is to be exposed.

25. The system of claim 17, said upper x-ray transmission window having:
an atomic number below 10;
structural rigidity to support up to 1/10 atm. of pressure without bowing more than approximately 100 microns;
substantial impermeability relative to said fluid;
x-ray transparency greater than 90% for characteristic photon energies from an element of interest for which a fluidic concentration is to be measured;
x-ray scattering therefrom minimized to less than approximately 10% of radiation scattered from a column of said fluid equal to one optical depth in said fluid of a characteristic photonic energy from an element of interest for which a fluidic concentration is to be measured; and
freedom from any single contaminant in excess of 1 part per million, when measured by x-ray fluorescence.

26. The system of claim 17, said upper x-ray transmission window comprising a polyimid film having structural rigidity to support up to 1/10 atm. of pressure without bowing more than approximately 100 microns.

27. The system of claim 17, further comprising:
voltage application means for applying a voltage differential between said upper high surface area electrode and said lower high surface area electrode while said fluid is flowing through said central flow interelectrode gap; and
x-ray source means positioned and aligned relative to said upper x-ray transmission window for exposing said preconcentration cell to x-rays substantially transmitted through said upper x-ray transmission window, while flowing said fluid and while applying said voltage differential.

28. The system of claim 17, further comprising:
x-ray source means positioned and aligned relative to said upper x-ray transmission window for emitting x-rays toward said preconcentration cell substantially transmitted through said upper x-ray transmission window; and
x-ray fluorescence detector means positioned and aligned relative to said upper x-ray transmission window for detecting fluoresced energy emitted by said preconcentration cell due to said emitting x-rays toward said preconcentration cell, through said upper x-ray transmission window.

29. The system of claim 28, further comprising:
x-ray fluorescence analysis means for analyzing the detected x-ray fluoresced energy and deducing therefrom a concentration in said fluid of at least one element of interest in said fluid.

30. The system of claim 1, said ionic preconcentration cell further comprising:
inlet flow means for entering a fluid into said ionic preconcentration cell and enabling said fluid to flow through said central flow interelectrode gap.

31. The system of claim 30, said inlet flow means comprising at least one planar inlet flow slot substantially coplanar with said central flow interelectrode gap.

32. The system of claim 30, said inlet flow means comprising a plurality of mutually-substantially coplanar inlet flow tubes substantially coplanar with said central flow interelectrode gap and substantially parallel with one another.

33. The system of claim 30, said inlet flow means comprising turbulence enhancement means for enhancing a turbulence of the flow of said fluid to induce mixing of said flow to enable uniform extraction of said at least one element from the flow stream.

34. The system of claim 30, said inlet flow means comprising access means for accessing said inlet flow means for physically cleaning debris therefrom.

35. The system of claim 1, said ionic preconcentration cell further comprising:
outlet flow means for exiting said fluid out from said ionic preconcentration cell after said fluid has flowed through said central flow interelectrode gap.

36. The system of claim 35, said outlet flow means comprising at least one outlet flow slot substantially coplanar with said central flow interelectrode gap.

37. The system of claim 35, said outlet flow means comprising a plurality of outlet flow tubes substantially coplanar with said central flow interelectrode gap and substantially parallel with one another.

38. The system of claim 35, said outlet flow means comprising access means for accessing said outlet flow means for physically cleaning debris therefrom.

39. The system of claim 1:
said upper high surface area electrode further having upper electrode thickness less than or equal to approximately $l=1/(\mu^*\rho)$, wherein:
l designates an optical depth of said upper high surface area electrode when wetted with an element of interest for which a fluidic concentration is to be measured, in said fluid;
$\mu$ designates a mass absorption coefficient of said upper high surface area electrode when wetted with said element of interest in said fluid; and
$\rho$ designates a material density of said upper high surface area electrode when wetted with said element of interest in said fluid.

40. The system of claim 39:
said lower high surface area electrode further having a lower electrode thickness less than or equal to approximately $l=1/(\mu^*\rho)$, wherein:
l designates an optical depth of said lower high surface area electrode when wetted with an element of interest for which a fluidic concentration is to be measured, in said fluid;
$\mu$ designates a mass absorption coefficient of said lower high surface area electrode when wetted with said element of interest in said fluid; and
$\rho$ designates a material density of said lower high surface area electrode when wetted with said element of interest in said fluid.

41. The system of claim 1, said upper high surface area electrode and said lower high surface area electrode further having an ordinary surface area approximately equal to an interrogation spot area of x-rays to which said preconcentration cell is to be exposed.

42. The system of claim 1:
said upper high surface area electrode and said lower high surface area electrode each comprising a high surface area material in turn having:
a large plurality of pores characterized by a specific surface area of at least approximately 100 m²/g;
an average pore diameter of said pores between approximately 30 nm and 10 nm per pore;
a distribution of the pore diameters grouped with a standard deviation of less than approximately 10 nm around said average pore diameter;
an x-ray transparency greater than approximately 90% for characteristic photon energies from an element of interest for which a fluidic concentration is to be measured;
electrical conductivity of 10–40 mOhms-cm when fabricated into a ¼ mm thick electrode;
the ability to contain approximately at least 0.1% by weight of foreign material relative to said high surface area material prior to saturation;
high structural rigidity wherein a displacement under the flow of said fluid does not exceed approximately 0.25 mm;
high wetting ability wherein an approximately ¼mm thick sheet of said high surface area material becomes substantially wetted in less than approximately three seconds; and
freedom from metallic impurities in excess of approximately 0.5 parts per million, when measured by x-ray fluorescence analysis.

43. The system of claim 42, said large plurality of pores characterized by a specific surface area of at least approximately 400 m²/g.

44. The system of claim 42, said large plurality of pores characterized by a specific surface area of at most approximately 1000 m²/g.

45. The system of claim 42, said large plurality of pores characterized by a specific surface area of at most approximately 1000 m²/g.

46. The system of claim 1, said upper high surface area electrode and said lower high surface area electrode each comprising a high surface area material in turn having:
an x-ray transparency greater than approximately 90% for characteristic photon energies from an element of interest for which a fluidic concentration is to be measured.

47. The system of claim 1, said upper high surface area electrode and said lower high surface area electrode each comprising a carbon aerogel.

48. The system of claim 1, said upper high surface area electrode having a thickness less than approximately l=1/($\mu^*\rho$); wherein:
l designates an optical depth of said upper high surface area electrode when wetted with said fluid;
$\mu$ designates a mass absorption coefficient of said high surface area electrode when wetted with said fluid; and
$\rho$ designates a density of said high surface area electrode when wetted with said fluid.

49. The system of claim 48, said lower high surface area electrode having a thickness less than approximately l=1/($\mu^*\rho$); wherein:
l designates an optical depth of said lower high surface area electrode when wetted with said fluid;
$\mu$ designates a mass absorption coefficient of said lower surface area electrode when wetted with said fluid; and
$\rho$ designates a density of said lower surface area electrode when wetted with said fluid.

50. The system of claim 1, said calibration data further comprising:
background data comprising data related to a rate at which photons be emitted from said preconcentration cell are detected, when said preconcentration cell is filled with a highly purified form of a fluid of interest and exposed to x-rays.

51. The system of claim 1, said calibration data further comprising:
sensitivity data related to a rate at which photons emitted from said preconcentration cell are detected, when said preconcentration cell is filled with a first calibration solution, containing at least one element of interest in a fluid of interest in known concentration above a minimum detection level of x-ray detection equipment to be used for said detecting and measuring, and when said preconcentration cell is exposed to x-rays.

52. The system of claim 1, further comprising:
flow control means for controlling a flow rate of said fluid through said ionic preconcentration cell so as to maintain $\epsilon$, which designates a predetermined percentage of at least one element of interest to be extracted from said fluid, below approximately 5% for said at least one element of interest.

53. The system of claim 52, wherein said $\epsilon$ is maintained below an extraction percentage selected from an extraction percentage group consisting of approximately 4%, 3%, 2%, and 1%.

54. The system of claim 1, further comprising:
leakage current monitoring means for monitoring a total non-saturated concentration of dissolved ions in said upper and lower high surface area electrodes, by monitoring a leakage current from said cell.

55. The system of claim 54, further comprising:
ultra-low trace measuring means for measuring at least one element of interest comprising ultra-low trace, high valence ions in said fluid, based on said detecting the non-saturated saturation state.

56. The system of claim 1, further comprising:
leakage current monitoring means for monitoring a total non-saturated concentration of dissolved ions in said upper and lower high surface area electrodes; and
flow rate adjustment means for adjusting the flow of said fluid through said ionic preconcentration cell to control a percentage of said ions extracted from said fluid, based on said monitoring of said leakage current by said leakage current monitoring means.

57. The system of claim 1, further comprising:
time control means for controlling how long said fluid flows through said ionic preconcentration cell based on setting an impurity concentration C, in a range where conductivity varies substantially linearly with concentration, to a predetermined desired concentration detection level and flowing said fluid for a time t given by:

$$t \propto \frac{Sl}{\sigma} \propto \frac{Sl}{C};$$

wherein:
S designates a sensitivity of x-ray detection equipment to be used for said detecting and measuring;
l designates a thickness of said upper high surface area electrode; and
$\sigma$ designates a composite conductivity of said fluid.

58. The system of claim 1, further comprising triggering means for triggering an action in response to said system detecting that a concentration of at least one element of interest in said fluid has passed a predetermined, non-saturated threshold concentration.

59. The system of claim 58, further comprising injection action means for injecting at least one element into said fluid, thereby maintaining said concentration within a predetermined concentration range, as said action in response to said triggering means.

60. The system of claim 58, further comprising dilution action means for diluting at least one diluting fluid into said fluid, thereby maintaining said concentration within a predetermined concentration range, as said action in response to said triggering means.

61. The system of claim 1, further comprising:
ionic release means for cleaning said preconcentration cell after use by releasing ions accumulated within said high specific surface area of said electrodes into said fluid, after the accumulated ions have been exposed to x-rays and fluorescence from said preconcentration cell has been detected.

62. The system of claim 1, further comprising:
a telecommunications link for downloading and analyzing said test data from said ionic preconcentration cell.

63. A method for identifying and measuring concentrations of elements in fluids, comprising the steps of:
flowing a fluid through a central flow interelectrode gap of an ionic preconcentration cell separating an upper high specific surface area electrode from a lower high specific surface area electrode of said ionic preconcentration cell by a predetermined interelectrode gap width;
applying a known voltage differential between said upper high surface area electrode and said lower high surface area electrode while said fluid is flowing through said central flow interelectrode gap;
exposing said cell to x-rays; and
deducing an identity, or measurement of concentration, of an unknown concentration of at least one element of interest in said a fluid of interest, based on comparing calibration data with test data related to a rate at which photons emitted from said preconcentration cell are detected based on said fluid of interest with said unknown concentration flowing through said central flow interelectrode gap at a known flow rate for a known period of time together with said applying said known voltage differential and said exposing said cell to x-rays, wherein said calibration data is obtained by:
flowing a fluid of interest containing a known concentration of at least one element of interest through said central flow interelectrode gap at a known rate for a known period of time;
applying a known voltage differential across said electrodes;
exposing the preconcentration cell to x-rays; and
acquiring data related to a rate at which photons emitted from said preconcentration cell are detected.

64. The method of claim 63, said step of applying said voltage differential further comprising the step of:
applying an electrostatic charge across said electrodes and thereby maintaining ions from said at least one element entrained in said electrodes during transport of said ionic preconcentration cell, using a transportable voltage supply.

65. The method of claim 64, further comprising the step of:
providing said transportable voltage supply embedded into a body of said ionic preconcentration cell.

66. The method of claim 63, further comprising the step of:
intimately contacting an upper surface of said upper high surface area electrode with an upper x-ray transmission window of said ionic preconcentration cell.

67. The method of claim 66, further comprising the step of:
intimately contacting a lower surface of said lower high surface area electrode with a lower x-ray transmission window of said ionic preconcentration cell.

68. The method of claim 67, further comprising the step of providing said lower x-ray transmission window having:
an atomic number below 10;
structural rigidity to support up to $1/10$ atm. of pressure without bowing more than approximately 100 microns;
substantial impermeability relative to said fluid;
x-ray transparency greater than 90% for characteristic photon energies from an element of interest for which a fluidic concentration is to be measured;
x-ray scattering therefrom minimized to less than approximately 10% of radiation scattered from a column of said fluid equal to one optical depth in said fluid of a characteristic photonic energy from an element of interest for which a fluidic concentration is to be measured; and
freedom from any single contaminant in excess of 1 part per million, when measured by x-ray fluorescence.

69. The method of claim 67, further comprising the step of:
providing said lower x-ray transmission window comprising a polyimid film having structural rigidity to support up to $1/10$ atm. of pressure without bowing more than approximately 100 microns.

70. The method of claim 66, further comprising the step of:
maintaining a position of said upper and lower high surface area electrodes and said upper x-ray transmission window relative to one another, using a body of said ionic preconcentration cell comprising a material having:
substantially no conductivity;
resistance to ionic leaching; and
resistance to radiation degradation from x-rays to which said preconcentration cell is to be exposed.

71. The method of claim 66, further comprising the step of:
maintaining a position of said upper and lower high surface area electrodes and said upper x-ray transmission window relative to one another, using a body of said ionic preconcentration cell comprising a material selected from a material group consisting of: plastic, glass, and fiberglass.

72. The method of claim 66, further comprising the step of:
maintaining a position of said upper and lower high surface area electrodes and said upper x-ray transmission window relative to one another, using a body of said ionic preconcentration cell comprising a material comprising a non-conducting, machinable polymer substantially resistant to radiation degradation.

73. The method of claim 66, further comprising the step of:
providing a surface area of said upper x-ray transmission window approximately equal to an interrogation spot area of x-rays to which said preconcentration cell is to be exposed.

74. The method of claim 66, further comprising the step of providing said upper x-ray transmission window having:
an atomic number below 10;
structural rigidity to support up to ⅒ atm. of pressure without bowing more than approximately 100 microns;
substantial impermeability relative to said fluid;
x-ray transparency greater than 90% for characteristic photon energies from an element of interest for which a fluidic concentration is to be measured;
x-ray scattering therefrom minimized to less than approximately 10% of radiation scattered from a column of said fluid equal to one optical depth in said fluid of a characteristic photonic energy from an element of interest for which a fluidic concentration is to be measured; and
freedom from any single contaminant in excess of 1 part per million, when measured by x-ray fluorescence.

75. The method of claim 66, further comprising the step of:
providing said upper x-ray transmission window comprising a polyimid film having structural rigidity to support up to ⅒ atm. of pressure without bowing more than approximately 100 microns.

76. The method of claim 66, further comprising the steps of:
emitting x-rays toward said preconcentration cell substantially transmitted through said upper x-ray transmission window; and
detecting fluoresced energy emitted by said preconcentration cell due to said emitting x-rays toward said preconcentration cell, through said upper x-ray transmission window.

77. The method of claim 76, further comprising the step of:
analyzing the detected x-ray fluoresced energy and deducing therefrom a concentration in said fluid of at least one element of interest in said fluid.

78. The method of claim 63, further comprising the steps of:
entering a fluid into said ionic preconcentration cell using inlet flow means therefor; and
enabling said fluid to flow through said central flow interelectrode gap.

79. The method of claim 78, said step of entering said fluid further comprising entering said fluid through said inlet flow means comprising at least one mutually-planar inlet flow slot substantially coplanar with said central flow interelectrode gap.

80. The method of claim 78, said step of entering said fluid further comprising entering said fluid through said inlet flow means comprising a plurality of substantially coplanar inlet flow tubes substantially coplanar with said central flow interelectrode gap and substantially parallel with one another.

81. The method of claim 78, further comprising the step of enhancing a turbulence of the flow of said fluid while entering said fluid, thereby inducing mixing of said flow for enabling uniform extraction of said at least one element from the flow stream.

82. The method of claim 78, further comprising the step of physically cleaning debris from said inlet flow means using access means for accessing said inlet flow means.

83. The method of claim 63, further comprising the step of:
exiting said fluid out from said ionic preconcentration cell after said fluid has flowed through said central flow interelectrode gap using outlet flow means therefor.

84. The method of claim 83, said step of exiting said fluid further comprising exiting said fluid through said outlet flow means comprising at least one outlet flow slot substantially coplanar with said central flow interelectrode gap.

85. The method of claim 83, said step of exiting said fluid further comprising exiting said fluid through said outlet flow means comprising a plurality of outlet flow tubes substantially coplanar with said central flow interelectrode gap and substantially parallel with one another.

86. The method of claim 83, further comprising the step of physically cleaning debris from said outlet flow means using access means for accessing said outlet flow means.

87. The method of claim 63, further comprising the step of:
providing said upper high surface area electrode with an upper electrode thickness thereof less than or equal to approximately $l=1/(\mu^*\rho)$, wherein:
l designates an optical depth of said upper high surface area electrode when wetted with an element of interest for which a fluidic concentration is to be measured, in said fluid;
$\mu$ designates a mass absorption coefficient of said upper high surface area electrode, when wetted with said element of interest in said fluid; and
$\rho$ designates a material density of said upper high surface area electrode, when wetted with said element of interest in said fluid.

88. The method of claim 87, further comprising the step of:
providing said lower high surface area electrode with a lower electrode thickness thereof less than or equal to approximately $l=1/(\mu^*\rho)$, wherein:
l designates an optical depth of said lower high surface area electrode when wetted with an element of interest for which a fluidic concentration is to be measured, in said fluid;
$\mu$ designates a mass absorption coefficient of said lower high surface area electrode, when wetted with said element of interest in said fluid; and
$\rho$ designates a material density of said lower high surface area electrode, when wetted with said element of interest in said fluid.

89. The method of claim 63, further comprising the step of:
providing ordinary surface areas of said upper high surface area electrode and said lower high surface area electrode approximately equal to an interrogation spot area of x-rays to which said preconcentration cell is to be exposed.

90. The method of claim 63, further comprising the step of:
providing said central flow interelectrode gap having said predetermined interelectrode gap width, designated d, within an interelectrode gap range specified by:

$$d = \frac{\sigma\Phi}{q\varepsilon}\frac{w_i}{w_f}\frac{A}{n_f CF} \times 100\% \approx 2 \times 10^{-9} \frac{\Phi w_i A}{q\varepsilon w_f n_f F} \times 100\% \propto \frac{\Phi A}{\varepsilon F};$$

$\epsilon$ designates a predetermined percentage of at least one element of interest to be extracted from said fluid, $\sigma$ designates a composite conductivity of said fluid, $\Phi$ designates said voltage differential applied across said electrodes, $q=1.60\times10^{-19}$ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, c designates a concentration of said at least one element of interest in said fluid, and F designates a flow rate of said fluid through said ionic preconcentration cell;

said high surface area electrodes further having said ordinary surface area A approximately equal to an interrogation spot area of x-rays to which said preconcentration cell is to be exposed;

said $\epsilon$ is chosen to be below approximately 5% for said at least one element of interest;

said $\Phi$ is chosen to be below an electrochemical potential of said at least one element of interest and below an electrolysis potential of said fluid;

said F is chosen to exert no more than approximately 0.1 atm of pressure upon an upper x-ray transmission window of said ionic preconcentration cell in intimate contact with an upper surface of said upper high surface area electrode;

said $n_f$ and said $w_f$ are chosen with reference to said at least one element of interest; and said $w_i$ is chosen with reference to said fluid.

91. The method of claim 90, further comprising the step of:

providing said central flow interelectrode gap having said predetermined interelectrode gap width, d, with:

a minimum gap width selected from a minimum gap width group consisting of 2 mm, 1 mm, 0.5 mm, and 0.25 mm; and a maximum gap width selected from a maximum gap width group consisting of 2 mm, 5 mm, and 10 mm.

92. The method of claim 63 further comprising the step of:
providing said upper high surface area electrode and said lower high surface area electrode each comprising a high surface area material in turn having:

a large plurality of pores characterized by a specific surface area of at least approximately 100 $m^2/g$;

an average pore diameter of said pores between approximately 30 nm and 10 nm per pore;

a distribution of the pore diameters grouped with a standard deviation of less than approximately 10 nm around said average pore diameter;

an x-ray transparency greater than approximately 90% for characteristic photon energies from an element of interest for which a fluidic concentration is to be measured;

electrical conductivity of 10–40 mOhms-cm when fabricated into a ¼ mm thick electrode;

the ability to contain approximately at least 0.1% by weight of foreign material relative to said high surface area material prior to saturation;

high structural rigidity wherein a displacement under the flow of said fluid does not exceed approximately 0.25 mm;

high wetting ability wherein an approximately ¼ mm thick sheet of said high surface area material becomes substantially wetted in less than approximately three seconds; and freedom from metallic impurities in excess of approximately 0.5 parts per million, when measured by x-ray fluorescence analysis.

93. The method of claim 92, said large plurality of pores characterized by a specific surface area of at least approximately 400 $m^2/g$.

94. The method of claim 93, said large plurality of pores characterized by a specific surface area of at most approximately 1000 $m^2/g$.

95. The method of claim 92, said large plurality of pores characterized by a specific surface area of at most approximately 1000 $m^2/g$.

96. The method of claim 63, further comprising the step of:

providing said upper high surface area electrode and said lower high surface area electrode each comprising a high surface area material in turn having:

an x-ray transparency greater than approximately 90% for characteristic photon energies from an element of interest for which a fluidic concentration is to be measured.

97. The method of claim 63, further comprising the step of:

providing said upper high surface area electrode and said lower high surface area electrode each comprising a carbon aerogel.

98. The method of claim 63, further comprising the step of:

providing said upper high surface area electrode with a thickness less than approximately $l=1/(\mu^*\rho)$; wherein:

l designates an optical depth of said upper high surface area electrode when wetted with said fluid;

$\mu$ designates a mass absorption coefficient of said high surface area electrode when wetted with said fluid; and $\rho$ designates a density of said high surface area electrode when wetted with said fluid.

99. The method of claim 98, further comprising the step of:

providing said lower high surface area electrode with a thickness less than approximately $l=1/(\mu^*\rho)$; wherein:

l designates an optical depth of said lower high surface area electrode when wetted with said fluid;

$\mu$ designates a mass absorption coefficient of said lower surface area electrode when wetted with said fluid; and $\rho$ designates a density of said lower surface area electrode when wetted with said fluid.

100. The method of claim 63, further comprising the step of obtaining said calibration data by:

filling said preconcentration cell with a highly purified form of a fluid of interest;

exposing the filled preconcentration cell to x-rays; and acquiring background data related to a rate at which photons emitted from said preconcentration cell are detected; and associating said background data with said preconcentration cell.

101. The method of claim 63, further comprising the step of obtaining said calibration data by:

filling said preconcentration cell, with a first calibration solution containing at least one element of interest in a fluid of interest in known concentration above a minimum detection level of x-ray detection equipment to be used for said detecting and measuring;

exposing the filled preconcentration cell to x-rays;

acquiring sensitivity data related to a rate at which photons emitted from said preconcentration cell are detected; and associating said sensitivity data with said preconcentration cell.

102. The method of claim 63, further comprising the step of obtaining said calibration data by:

applying said voltage differential across the electrodes of said preconcentration cell, below an electrochemical potential of said at least one element of interest and below an electrolysis potential of a calibration solution;

flowing said calibration solution containing said at least one element of interest in a fluid of interest in known concentration below a minimum detection level of x-ray detection equipment to be used for said detecting and measuring through the central flow interelectrode gap of said preconcentration cell at a substantially constant flow rate;

exposing said preconcentration cell with said calibration solution therein to x-rays;

acquiring ion extraction rate data related to a rate at which photons emitted from said preconcentration cell are detected; and associating said ion extraction rate data with said preconcentration cell.

103. The method of claim 63, further comprising the step of obtaining said calibration data by:
filling said preconcentration cell, with a highly purified form of a fluid of interest;
exposing the filled preconcentration cell to x-rays;
acquiring background data related to a rate at which photons emitted from said preconcentration are detected cell;
filling said preconcentration cell, with a first calibration solution containing at least one element of interest in said fluid of interest in known concentration above a minimum detection level of x-ray detection equipment to be used for said detecting and measuring;
exposing the filled preconcentration cell to x-rays;
acquiring sensitivity data related to a rate at which photons emitted from said preconcentration cell are detected;
applying said voltage differential across the electrodes of said preconcentration cell, below an electrochemical potential of said at least one element of interest and below an electrolysis potential of a second calibration solution;
flowing said second calibration solution containing said at least one element of interest in said fluid of interest in known concentration below a minimum detection level of x-ray detection equipment to be used for said detecting and measuring through the central flow interelectrode gap of said preconcentration cell, at a substantially constant flow rate;
exposing said preconcentration cell with said second calibration solution therein to x-rays;
acquiring ion extraction rate data related to a rate at which photons emitted from of said preconcentration cell are detected; and
associating said background data, said sensitivity data, and said ion extraction rate data with said preconcentration cell.

104. The method of claim 103, further comprising the steps of:
applying said voltage differential across said electrodes below an electrochemical potential of said at least one element of interest and below an electrolysis potential of said fluid, suspected to contain at least one element of interest;
flowing said fluid through said central flow interelectrode gap at a substantially constant flow rate;
exposing said preconcentration cell with said fluid therein to x-rays; and
acquiring said test data related to a rate at which photons emitted from said preconcentration cell are detected.

105. The method of claim 104, further comprising the step of:
analyzing said test data in relation to said background data, said sensitivity data, and said ion extraction rate data, and deducing therefrom a concentration in said fluid, if any, of the suspected at least one element of interest.

106. The method of claim 63, further comprising the steps of:
applying said voltage differential across said electrodes below an electrochemical potential of said at least one element of interest and below an electrolysis potential of said fluid, suspected to contain at least one element of interest;
flowing said fluid through said central flow interelectrode gap at a substantially constant flow rate;
exposing said preconcentration cell with said fluid therein to x-rays; and
acquiring said test data related to a rate at which photons emitted from said preconcentration cell are detected.

107. The method of claim 106, further comprising the step of:
analyzing said test data and deducing therefrom a concentration in said fluid, if any, of the suspected at least one element of interest.

108. The method of claim 63, further comprising the step of:
exposing said preconcentration cell to x-rays substantially transmitted through said upper x-ray transmission window, while flowing said fluid and while applying said voltage differential.

109. The method of claim 63, said step of applying said voltage differential further comprising the steps of:
ceasing flow of said fluid while applying an electrostatic charge across said electrodes and thereby maintaining ions from said at least one element entrained in said electrodes;
transporting said ionic preconcentration cell to an x-ray source means for emitting x-rays toward said preconcentration cell while applying said electrostatic charge; and
exposing said preconcentration cell to x-rays from said x-ray source means while applying said electrostatic charge.

110. The method of claim 63, further comprising the step of:
controlling a flow rate of said fluid through said ionic preconcentration cell so as to maintain ϵ, which designates a predetermined percentage of at least one element of interest to be extracted from said fluid, below approximately 5% for said at least one element of interest.

111. The method of claim 110, further comprising the step of:
maintaining said ϵ below an extraction percentage selected from an extraction percentage group consisting of approximately 4%, 3%, 2%, and 1%.

112. The method of claim 63, further comprising the step of:
controlling a flow rate F of said fluid through said ionic preconcentration cell and maintaining said F at a substantially constant level so as to maintain ϵ, which designates a predetermined percentage of at least one element of interest to be extracted from said fluid and is specified by:

$$\varepsilon = \frac{\Gamma_{is}}{\Gamma_{is}} = \frac{\sigma \Phi}{qd} \frac{w_i}{w_f} \frac{A}{n_f CF} \times 100\%,$$

below approximately 5% for said at least one element of interest; wherein:

$\Gamma_{ie}$ and $\Gamma_{is}$ designate rates at which ions of said at least one element of interest are respectively extracted from said fluid by said cell and supplied to said cell by said fluid, σ designates a composite conductivity of said fluid, Φ designates said voltage differential applied across said electrodes, d designates said predetermined interelectrode gap width of said central flow interelectrode gap, $q=1.60\times10^{-19}$ Coulomb designates the unit charge, A designates an ordinary surface area covered by said electrodes, $n_f$ designates a number density of said fluid, $w_i$ and $W_f$ designate atomic/molecular weights, respectively, of said at least one element of interest and of said fluid, and c designates a concentration of said at least one element of interest in said fluid; and having said concentration c in a range where conductivity varies substantially linearly with concentration, with c in units of parts per billion, wherein σ is approximated by:

$\sigma \approx 2\times10^{-9}$ C/Ohm-cm.

113. The method of claim 112, further comprising the step of:

maintaining said ε below an extraction percentage selected from an extraction percentage group consisting of approximately 4%, 3%, 2%, and 1%.

114. The method of claim 63, further comprising the step of:

applying said voltage differential across said electrodes below an electrochemical potential of at least one element of interest and below an electrolysis potential of said fluid.

115. The method of claim 63, further comprising the step of:

monitoring a total non-saturated concentration of dissolved ions in said upper and lower high surface area electrodes, by monitoring a leakage current from said cell.

116. The method of claim 115, further comprising the step of:

measuring at least one element of interest comprising ultra-low trace, high valence ions in said fluid, based on said detecting the non-saturated saturation state.

117. The method of claim 63, further comprising the steps of:

monitoring a total non-saturated concentration of dissolved ions in said upper and lower high surface area electrodes by monitoring a leakage current in said cell; and adjusting the flow of said fluid through said ionic preconcentration cell to control a percentage of said ions extracted from said fluid, based on said monitoring of said leakage current.

118. The method of claim 63, further comprising the steps of:

setting an impurity concentration C, in a range where conductivity varies substantially linearly with concentration, to a predetermined desired concentration detection level; and controlling how long said fluid flows through said ionic preconcentration cell by flowing said fluid for a time t given by:

$$t \propto \frac{Sl}{\sigma} \propto \frac{Sl}{C},$$

S designates a sensitivity of x-ray detection equipment to be used for said detecting and measuring;

l designates a thickness of said upper high surface area electrode; and

σ designates a composite conductivity of said fluid.

119. The method of claim 63, further comprising the step of:

triggering an action in response to detecting that a concentration of at least one element of interest in said fluid has passed a predetermined, non-saturated threshold concentration.

120. The method of claim 119, said step of triggering further comprising the step of:

maintaining said concentration within a predetermined concentration range by injecting at least one element into said fluid as said action in response to said detecting.

121. The method of claim 119, said step of triggering further comprising the step of:

maintaining said concentration within a predetermined concentration range by diluting at least one diluting fluid into said fluid as said action in response to said detecting.

122. The method of claim 63, further comprising the step of:

cleaning said preconcentration cell after use by releasing ions accumulated within said high specific surface area of said electrodes into said fluid, after the accumulated ions have been exposed to x-rays and fluorescence from said preconcentration cell has been detected.

123. The method of claim 63, further comprising the step of:

downloading and analyzing said test data from said ionic preconcentration cell using a telecommunications link.

124. An ionic preconcentration cell apparatus for identifying and measuring concentrations of elements in fluids, comprising:

an upper high surface area electrode having a high specific surface area thereof;

a lower high surface area electrode having a high specific surface area thereof, substantially parallel to said upper high surface area electrode;

a central flow interelectrode gap separating said upper and lower high surface area electrodes by a predetermined interelectrode gap width;

fluid flow means for flowing a fluid through said central flow interelectrode gap; and an upper x-ray transmission window in intimate contact with an upper surface of said upper high surface area electrode; said upper x-ray transmission window having:

an atomic number below 10;

structural rigidity to support up to 1/10 atm. of pressure without bowing more than approximately 100 microns;

substantial impermeability relative to said fluid;

x-ray transparency greater than 90% for characteristic photon energies from an element of interest for which a fluidic concentration is to be measured;

x-ray scattering therefrom minimized to less than approximately 10% of radiation scattered from a column of said fluid equal to one optical depth in said fluid of a characteristic photonic energy from an element of interest for which a fluidic concentration is to be measured; and freedom from any single contaminant in excess of 1 part per million, when measured by x-ray fluorescence.

125. An ionic preconcentration cell apparatus for identifying and measuring concentrations of elements in fluids, comprising:

an upper high surface area electrode having a high specific surface area thereof;

a lower high surface area electrode having a high specific surface area thereof, substantially parallel to said upper high surface area electrode;

a central flow interelectrode gap separating said upper and lower high surface area electrodes by a predetermined interelectrode gap width;

fluid flow means for flowing a fluid through said central flow interelectrode gap;

an upper x-ray transmission window in intimate contact with an upper surface of said upper high surface area electrode; and a lower x-ray transmission window in intimate contact with a lower surface of said lower high surface area electrode; said lower x-ray transmission window having:

an atomic number below 10;

structural rigidity to support up to 1/10 atm. of pressure without bowing more than approximately 100 microns;

substantial impermeability relative to said fluid;

x-ray transparency greater than 90% for characteristic photon energies from an element of interest for which a fluidic concentration is to be measured;

x-ray scattering therefrom minimized to less than approximately 10% of radiation scattered from a column of said fluid equal to one optical depth in said fluid of a characteristic photonic energy from an element of interest for which a fluidic concentration is to be measured; and freedom from any single contaminant in excess of 1 part per million, when measured by x-ray fluorescence.

126. A method for identifying and measuring concentrations of elements in fluids, comprising the steps of:

flowing a fluid through a central flow interelectrode gap of an ionic preconcentration cell separating an upper high specific surface area electrode from a lower high specific surface area electrode of said ionic preconcentration cell by a predetermined interelectrode gap width;

applying a voltage differential between said upper high surface area electrode and said lower high surface area electrode while said fluid is flowing through said central flow interelectrode gap;

passing x-rays through an upper x-ray transmission window intimately contacting an upper surface of said upper high surface area electrode;

deducing an identity, or measurement of concentration, of at least one element in said fluid based on a response of said preconcentration cell to said x-rays; and providing said upper x-ray transmission window having:

an atomic number below 10;

structural rigidity to support up to 1/10 atm. of pressure without bowing more than approximately 100 microns;

substantial impermeability relative to said fluid;

x-ray transparency greater than 90% for characteristic photon energies from an element of interest for which a fluidic concentration is to be measured by said method;

x-ray scattering therefrom minimized to less than approximately 10% of radiation scattered from a column of said fluid equal to one optical depth in said fluid of a characteristic photonic energy from an element of interest for which a fluidic concentration is to be measured by said method; and freedom from any single contaminant in excess of 1 part per million, when measured by x-ray fluorescence.

127. A method for identifying and measuring concentrations of elements in fluids, comprising the steps of:

flowing a fluid through a central flow interelectrode gap of an ionic preconcentration cell separating an upper high specific surface area electrode from a lower high specific surface area electrode of said ionic preconcentration cell by a predetermined interelectrode gap width;

applying a voltage differential between said upper high surface area electrode and said lower high surface area electrode while said fluid is flowing through said central flow interelectrode gap;

passing x-rays through an upper x-ray transmission window intimately contacting an upper surface of said upper high surface area electrode;

deducing an identity, or measurement of concentration, of at least one element in said fluid based on a response of said preconcentration cell to said x-rays;

passing said x-rays through a lower x-ray transmission window intimately contacting a lower surface of said lower high surface area electrode; and providing said lower x-ray transmission window having:

an atomic number below 10;

structural rigidity to support up to 1/10 atm. of pressure without bowing more than approximately 100 microns;

substantial impermeability relative to said fluid;

x-ray transparency greater than 90% for characteristic photon energies from an element of interest for which a fluidic concentration is to be measured by said method;

x-ray scattering therefrom minimized to less than approximately 10% of radiation scattered from a column of said fluid equal to one optical depth in said fluid of a characteristic photonic energy from an element of interest for which a fluidic concentration is to be measured by said method; and freedom from any single contaminant in excess of 1 part per million, when measured by x-ray fluorescence.

128. A method of optimizing fabrication of an ionic preconcentration cell for identifying and measuring concentrations of elements in fluids; said ionic preconcentration cell comprising an upper high surface area electrode having a high specific surface area thereof; a lower high surface area electrode having a high specific surface area thereof; and a central flow interelectrode gap separating said upper and lower high surface area electrodes by a predetermined interelectrode gap width; said method comprising the step of:

optimizing said upper high surface area electrode with an upper electrode thickness less than or equal to approximately an optical depth l of said upper high surface area electrode when wetted with a fluid to be flowed through said cell.

129. The optimization method of claim 128, wherein:

said $l=1/(\mu^*\rho)$; and wherein:

$\mu$ designates a mass absorption coefficient of said upper high surface area electrode when wetted with said fluid; and $\rho$ designates a material density of said upper high surface area electrode when wetted with said fluid.

130. The optimization method of claim 128, further comprising the step of:
optimizing said lower high surface area electrode with a lower electrode thickness less than or equal to approximately an optical depth l of said lower high surface area electrode when wetted with said fluid.

131. The optimization method of claim 130, wherein:
said l=1/($\mu$*$\rho$); and wherein:
$\mu$ designates a mass absorption coefficient of said lower high surface area electrode when wetted with said fluid; and
$\rho$ designates a material density of said lower high surface area electrode when wetted with said fluid.

132. A method of optimizing fabrication of an ionic preconcentration cell for identifying and measuring concentrations of elements in fluids; said ionic preconcentration cell comprising an upper high surface area electrode having a high specific surface area thereof; a lower high surface area electrode having a high specific surface area thereof; and a central flow interelectrode gap separating said upper and lower high surface area electrodes by a predetermined interelectrode gap width; said method comprising the step of:
optimizing said upper high surface area electrode with an upper electrode thickness less than or equal to approximately an optical depth l of said upper high surface area electrode when wetted with an element of interest for which a fluidic concentration is to be measured by said cell, in a fluid to be flowed through said cell.

133. The optimization method of claim 132, wherein:
said l=1/($\mu$*$\rho$); and wherein:
$\mu$ designates a mass absorption coefficient of said upper high surface area electrode when wetted with said element of interest in said fluid; and
$\rho$ designates a material density of said upper high surface area electrode when wetted with said element of interest in said fluid.

134. The optimization method of claim 132, further comprising the step of:
optimizing said lower high surface area electrode with a lower electrode thickness less than or equal to approximately an optical depth l of said lower high surface area electrode when wetted with said element of interest, in said fluid.

135. The optimization method of claim 134, wherein:
said l=1/($\mu$*$\rho$); and wherein:
$\mu$ designates a mass absorption coefficient of said lower high surface area electrode when wetted with said element of interest in said fluid; and
$\rho$ designates a material density of said lower high surface area electrode when wetted with said element of interest in said fluid.

136. A method of optimizing fabrication of an ionic preconcentration cell for identifying and measuring concentrations of elements in fluids; said ionic preconcentration cell comprising an upper high surface area electrode having a high specific surface area thereof; a lower high surface area electrode having a high specific surface area thereof; and a central flow interelectrode gap separating said upper and lower high surface area electrodes by a predetermined interelectrode gap width; said method comprising the step of:
optimizing said central flow interelectrode gap having said predetermined interelectrode gap width, designated d, within an interelectrode gap range specified by:

$$d = \frac{\sigma \Phi}{q\varepsilon} \frac{w_i}{w_f} \frac{A}{n_f CF} \times 100\% \approx 2 \times 10^{-9} \frac{\Phi w_i A}{q\varepsilon w_f n_f F} \times 100\% \propto \frac{\Phi A}{\varepsilon F};$$

wherein:
$\varepsilon$ designates a predetermined percentage of at least one element of interest to be extracted from a fluid to be flowed through said cell, $\sigma$ designates a composite conductivity of said fluid, $\Phi$ designates a voltage differential applied across said electrodes, q=1.60×10$^{-19}$ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, c designates a concentration of said at least one element of interest in said fluid, and F designates a flow rate of said fluid through said ionic preconcentration cell;
said high surface area electrodes further having said ordinary surface area A approximately equal to an interrogation spot area of x-rays to which said preconcentration cell is to be exposed;
said $\varepsilon$ is chosen to be below approximately 5% for said at least one element of interest;
said $\Phi$ is chosen to be below an electrochemical potential of said at least one element of interest and below an electrolysis potential of said fluid;
said F is chosen to exert no more than approximately 0.1 atm of pressure upon an upper x-ray transmission window of said ionic preconcentration cell in intimate contact with an upper surface of said upper high surface area electrode;
said $n_f$ and said $w_f$ are chosen with reference to said at least one element of interest; and
said $w_i$ is chosen with reference to said fluid.

137. The optimization method of claim 136, wherein:
as a consequence of said optimizing, said central flow interelectrode gap having said predetermined interelectrode gap width, d, with:
a minimum gap width selected from a minimum gap width group consisting of 2 mm, 1 mm, 0.5 mm, and 0.25 mm; and
a maximum gap width selected from a maximum gap width group consisting of 2 mm, 5 mm, and 10 mm.

138. An ionic preconcentration cell apparatus for identifying and measuring concentrations of elements in fluids, comprising:
an upper high surface area electrode having a high specific surface area thereof;
a lower high surface area electrode having a high specific surface area thereof, substantially parallel to said upper high surface area electrode;
a central flow interelectrode gap separating said upper and lower high surface area electrodes by a predetermined interelectrode gap width;
fluid flow means for flowing a fluid through said central flow interelectrode gap; and
flow control means for controlling a flow rate of said fluid through said ionic preconcentration cell so as to maintain $\varepsilon$, which designates a predetermined percentage of at least one element of interest to be extracted from said fluid, below approximately 5% for said at least one element of interest.

139. The apparatus of claim 138, wherein said ε is maintained below an extraction percentage selected from an extraction percentage group consisting of approximately 4%, 3%, 2%, and 1%.

140. The apparatus of claim 138, further comprising:
voltage application means for applying a voltage differential between said upper high surface area electrode and said lower high surface area electrode while said fluid is flowing through said central flow interelectrode gap; and
said flow control means for controlling said flow rate F of said fluid through said ionic preconcentration cell and maintaining said F at a substantially constant level so as to maintain said ε, which is specified by:

$$\varepsilon = \frac{\Gamma_{ie}}{\Gamma_{is}} = \frac{\sigma \Phi}{qd} \frac{w_i}{w_f} \frac{A}{n_f CF} \times 100\%,$$

below approximately 5% for said at least one element of interest; wherein:
$\Gamma_{ie}$ and $\Gamma_{is}$ designate rates at which ions of said at least one element of interest are respectively extracted from said fluid by said cell and supplied to said cell by said fluid, σ designates a composite conductivity of said fluid, Φ designates a potential applied by said voltage application means across said electrodes, d designates said predetermined interelectrode gap width of said central flow interelectrode gap, q=1.60×10⁻¹⁹ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, and c designates a concentration of said at least one element of interest in said fluid; and
for having said concentration c in a range where conductivity varies substantially linearly with concentration, with c in units of parts per billion, wherein σ is approximated by:

σ≈2×10⁻⁹ C/Ohm-cm.

141. The apparatus of claim 140, wherein said ε is maintained below an extraction percentage selected from an extraction percentage group consisting of approximately 4%, 3%, 2%, and 1%.

142. A method for identifying and measuring concentrations of elements in fluids, comprising the steps of:
flowing a fluid through a central flow interelectrode gap of an ionic preconcentration cell separating an upper high specific surface area electrode from a lower high specific surface area electrode of said ionic preconcentration cell by a predetermined interelectrode gap width;
applying a voltage differential between said upper high surface area electrode and said lower high surface area electrode while said fluid is flowing through said central flow interelectrode gap;
exposing said cell to x-rays;
deducing an identity, or measurement of concentration, of at least one element in said fluid based on a response of said preconcentration cell to said x-rays; and
controlling a flow rate of said fluid through said ionic preconcentration cell so as to maintain ε, which designates a predetermined percentage of at least one element of interest to be extracted from said fluid, below approximately 5% for said at least one element of interest.

143. The method of claim 142, further comprising the step of:
maintaining said ε below an extraction percentage selected from an extraction percentage group consisting of approximately 4%, 3%, 2%, and 1%.

144. The method of claim 142, said step of controlling said flow rate further comprising the step of:
controlling said flow rate F of said fluid through said ionic preconcentration cell and maintaining said F at a substantially constant level so as to maintain said ε, which is specified by:

$$\varepsilon = \frac{\Gamma_{ie}}{\Gamma_{is}} = \frac{\sigma \Phi}{qd} \frac{w_i}{w_f} \frac{A}{n_f CF} \times 100\%,$$

below approximately 5% for said at least one element of interest; wherein:
$\Gamma_{ie}$ and $\Gamma_{is}$ designate rates at which ions of said at least one element of interest are respectively extracted from said fluid by said cell and supplied to said cell by said fluid, σ designates a composite conductivity of said fluid, Φ designates said voltage differential applied across said electrodes, d designates said predetermined interelectrode gap width of said central flow interelectrode gap, q=1.60×10⁻¹⁹ Coulomb designates the unit charge, A designates an ordinary surface area covered by said electrodes, $n_f$ designates a number density of said fluid, $w_i$ and $w_f$ designate atomic/molecular weights, respectively, of said at least one element of interest and of said fluid, and C designates a concentration of said at least one element of interest in said fluid; and
having said concentration c in a range where conductivity varies substantially linearly with concentration, with c in units of parts per billion, wherein σ is approximated by:

σ≈2×10⁻⁹ C/Ohm-cm.

145. The method of claim 144, further comprising the step of:
maintaining said ε below an extraction percentage selected from an extraction percentage group consisting of approximately 4%, 3%, 2%, and 1%.

146. An ionic preconcentration cell apparatus for identifying and measuring concentrations of elements in fluids, comprising:
an upper high surface area electrode having a high specific surface area thereof;
a lower high surface area electrode having a high specific surface area thereof, substantially parallel to said upper high surface area electrode;
a central flow interelectrode gap separating said upper and lower high surface area electrodes by a predetermined interelectrode gap width;
fluid flow means for flowing a fluid through said central flow interelectrode gap; and
time control means for controlling how long said fluid flows through said ionic preconcentration cell based on setting an impurity concentration C, in a range where conductivity varies substantially linearly with concentration, to a predetermined desired concentration detection level and flowing said fluid for a time t given by:

$$t \propto \frac{Sl}{\sigma} \propto \frac{Sl}{C},$$

S designates a sensitivity of x-ray detection equipment to be used for said detecting and measuring;

l designates a thickness of said upper high surface area electrode; and

σ designates a composite conductivity of said fluid.

147. A method for identifying and measuring concentrations of elements in fluids, comprising the steps of:

flowing a fluid through a central flow interelectrode gap of an ionic preconcentration cell separating an upper high specific surface area electrode from a lower high specific surface area electrode of said ionic preconcentration cell by a predetermined interelectrode gap width;

applying a voltage differential between said upper high surface area electrode and said lower high surface area electrode while said fluid is flowing through said central flow interelectrode gap;

exposing said cell to x-rays;

deducing an identity, or measurement of concentration, of at least one element in said fluid based on a response of said preconcentration cell to said x-rays;

setting an impurity concentration C, in a range where conductivity varies substantially linearly with concentration, to a predetermined desired concentration detection level; and controlling how long said fluid flows through said ionic preconcentration cell by flowing said fluid for a time t given by:

$$t \propto \frac{Sl}{\sigma} \propto \frac{Sl}{C},$$

wherein:

S designates a sensitivity of x-ray detection equipment to be used for said identifying and measuring;

l designates a thickness of said upper high surface area electrode; and

σ designates a composite conductivity of said fluid.

* * * * *